(12) United States Patent
Kawamura

(10) Patent No.: US 6,969,612 B2
(45) Date of Patent: *Nov. 29, 2005

(54) REAGENT AND METHOD FOR MEASURING A CONCENTRATION OF PROTEIN

(75) Inventor: Tatsurou Kawamura, Kyotanabe (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 658 days.

This patent is subject to a terminal disclaimer.

(21) Appl. No.: 09/749,816

(22) Filed: Dec. 28, 2000

(65) Prior Publication Data

US 2001/0006819 A1   Jul. 5, 2001

(30) Foreign Application Priority Data

Dec. 28, 1999  (JP) .................................. 11-374752
Apr. 25, 2000  (JP) ............................. 2000-124904

(51) Int. Cl.$^7$ .......................................... G01N 33/00
(52) U.S. Cl. ......................................... 436/86; 436/89
(58) Field of Search .......................... 436/86, 172, 164, 436/89

(56) References Cited

U.S. PATENT DOCUMENTS

| | | | |
|---|---|---|---|
| 4,090,919 A | | 5/1978 | Chibata et al. |
| 4,201,471 A | | 5/1980 | Pitt et al. ...................... 356/70 |
| 4,203,724 A | * | 5/1980 | Sawai et al. ................. 436/519 |
| 4,485,176 A | | 11/1984 | Bollin, Jr. et al. |
| 4,684,252 A | | 8/1987 | Makiguchi et al. |
| 4,766,080 A | | 8/1988 | Fleming |
| 5,178,831 A | | 1/1993 | Sakota et al. |
| 5,212,099 A | * | 5/1993 | Marcus ....................... 436/172 |
| 5,264,589 A | * | 11/1993 | Corey ......................... 548/511 |
| 5,478,748 A | | 12/1995 | Akins, Jr. et al. |
| 5,658,532 A | * | 8/1997 | Kurosaki et al. .............. 422/64 |
| 5,922,609 A | * | 7/1999 | Kellner et al. .............. 436/103 |
| 6,036,922 A | * | 3/2000 | Kawamura et al. ...... 422/82.09 |
| 6,297,057 B1 | * | 10/2001 | Kawamura et al. ........... 436/86 |

FOREIGN PATENT DOCUMENTS

| | | |
|---|---|---|
| EP | 0 751 388 | 1/1997 |
| EP | 0 805 352 | 11/1997 |
| EP | 0 845 673 | 6/1998 |
| GB | 755900 | 8/1956 |
| JP | 58209946 | 12/1983 |
| JP | 07138119 | 5/1995 |
| JP | 9-145605 | 6/1997 |
| JP | 11133022 | 5/1999 |

* cited by examiner

Primary Examiner—Monique T. Cole
(74) Attorney, Agent, or Firm—McDermott Will & Emery LLP

(57) ABSTRACT

The object of the present invention is to measure a concentration of protein stably at a temperature not higher than 25° C., which is a possible ambient temperature at home, and further to expand the measurable concentration range while preventing an obstruction due to a suspending particle such as a bubble and the like, using a reagent prepared by mixing an acid in a solution containing tannin, tannic acid and m-galloyl gallic acid. By mixing the reagent in a solution to be detected to opacify the solution, intensities of at least a transmitted light or a scattered light of the solution to be detected is measured, and a protein concentration thereof is determined based on the intensity. The present invention also provides a method for measuring a concentration of a solution and a method of urinalysis, wherein a protein concentration is measured after measuring an angle of rotation.

26 Claims, 14 Drawing Sheets

Time elapsed after mixing of reagent (second)

REAGENT AND METHOD FOR MEASURING A CONCENTRATION OF PROTEIN

BACKGROUND OF THE INVENTION

The present invention relates to a method for measuring a concentration of a solute dissolved in a solution to be detected, and more particularly to a method for measuring a concentration of protein and that of any optical active substance other than protein.

As a conventional method for measuring a concentration of protein, there has been a method in which trichloroacetic acid is mixed in a solution to be detected to coagulate protein, thereby opacifying the solution, and the protein concentration is determined from the resulting turbidity. However, with such method, it is difficult to stably opacify the solution to be detected at a temperature of 25° C. or higher. Therefore, it is sometimes impossible to carry out the measurement at a temperature of 25 to 40° C., which is a normal ambient temperature at home.

As a conventional apparatus for urinalysis, there has been an apparatus in which a test paper or the like impregnated with a reagent is dipped in a urine, and a color reaction thereof is observed by a spectroscope or the like to detect the components of the urine. The test papers used herein have been required to be individually produced according to respective inspection items such as glucose and protein.

It is therefore an object of the present invention to solve the above problem. Namely, it is an object of the present invention to provide a method for measuring a protein concentration, which is highly stable and easy to maintain and manage at a temperature of 0 to 40° C., or an ambient temperature at home, and a reagent to be used therefor.

It is another object of the present invention to provide a method for enabling a simple and highly accurate urinalysis.

BRIEF SUMMARY OF THE INVENTION

In order to solve the above-described problem, the method for measuring a protein concentration in accordance with the present invention is characterized by using one reagent selected from the group consisting of tannin, tannic acid and m-galloyl gallic acid as a reagent for changing the optical characteristics of protein only.

Further, the method for measuring a protein concentration in accordance with the present invention is characterized by adding a pH controlling agent in a solution to be detected to regulate a pH of the solution to be detected to 1.5 to 5.8.

The method for measuring a protein concentration in accordance with the present invention comprises the steps of measuring intensities of at least a transmitted light or a scattered light of a solution to be detected before and after mixing therein the reagent, and determining a protein concentration in the solution to be detected based on the intensities.

Herein, it is preferable that a protein concentration in a solution to be detected in a low concentration range is determined from the scattered light intensity, and that of a solution to be detected in a high concentration range is determined from the transmitted light intensity.

The presence or absence of an erroneous measurement due to a suspending particle such as a bubble in the solution to be detected can be detected by comparing the intensity of the transmitted light with that of the scattered light.

Moreover, the present invention provides a method for measuring a concentration of a solution comprising the steps of measuring intensities of at least a transmitted light or a scattered light of a solution to be detected before and after mixing therein the reagent, measuring an angle of rotation of the solution to be detected before mixing therein the reagent, determining a protein concentration in the solution to be detected based on the intensities of at least the transmitted light or the scattered light, and determining a concentration of any optical active substance in the solution to be detected other than the protein from the protein concentration and the angle of rotation.

This method for measuring a concentration of a solution employs the same principle as that of the above-mentioned method for measuring a protein concentration. Thus, it uses one reagent selected from the group consisting of tannin, tannic acid and m-galloyl gallic acid as a reagent. In addition, a pH of the solution to be detected is regulated in the same manner.

While the novel features of the invention are set forth particularly in the appended claims, the invention, both as to organization and content, will be better understood and appreciated, along with other objects and features thereof, from the following detailed description taken in conjunction with the drawings.

DETAILED DESCRIPTION OF THE INVENTION

Figure 1:
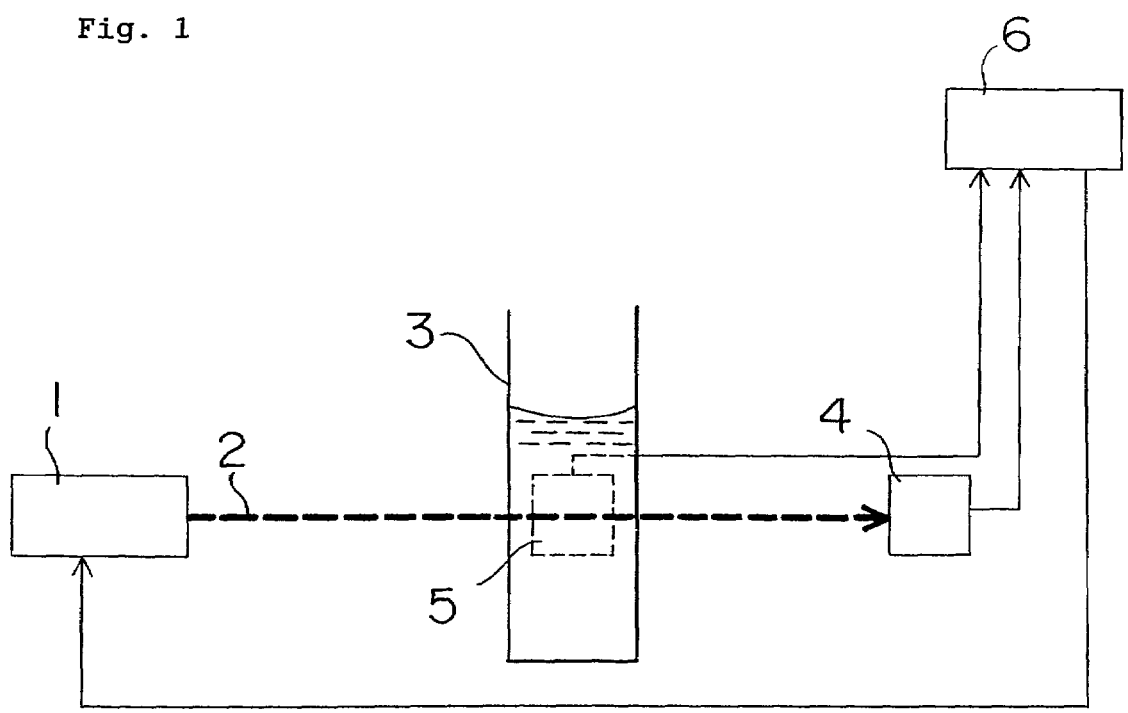
FIG. 1 is a side view schematically showing the configuration of a measurement apparatus used in an embodiment of the present invention.

The tannin reagent used in the measurement of a protein concentration in accordance with the present invention is a generic term for complicated aromatic compounds widely distributed in the plant kingdom having many phenol hydroxyl groups (Dictionary of Chemistry, Tokyo Kagaku Dojin), and the molecular weights thereof are from 600 to 2000 (Encyclopaedia Chimica, Kyoritsu Shuppan).

Tannic acid is a substance represented by the formula $C_{76}H_{52}O_{46}$ having a CAS Registry Number of 1401-55-4. m-galloyl gallic acid is a substance represented by the formula $C_{14}H_{10}O_9$ having a CAS Registry Number of 536-08-3.

These reagents react with protein in a solution to be detected to cause a turbidity corresponding to the protein concentration. The protein concentration of a solution to be detected can be measured by mixing therein these reagents. For example, when a urine is used as a solution to be detected, these reagents are mixed in the urine to coagulate the protein component, thereby changing the optical characteristics. Then, the protein concentration in the solution to be detected is determined from the difference between the scattered light intensities before and after mixing of the reagent ((the scattered light intensity after mixing of the reagent)−(the scattered light intensity before mixing of the reagent)) and/or from the ratio of the transmitted light intensity after mixing of the reagent to that before mixing of the reagent ((the transmitted light intensity after mixing of the reagent)/(the transmitted light intensity before mixing of the reagent)).

Herein, when the protein concentration is high (approximately 250 to 500 mg/dl or higher), there are cases where the protein does not coagulate at all or does not coagulate corresponding to the concentration. In these cases, it is sometimes impossible to measure the protein concentration because protein does not opacify at all or does not cause turbidity corresponding to the concentration. Even in such cases where measurement cannot be conducted, it is possible to opacify the protein by mixing a pH controlling agent in the solution to regulate the pH thereof after mixing of the pH controlling agent to 1.5 to 5.8.

It should be noted that the above reagents used in the present invention sometimes function as a pH controlling agent. In such a case, addition of a pH controlling agent is not necessary.

In this manner, even when a protein concentration is high, turbidity can be caused corresponding to the protein concentration, and therefore the protein concentration can be measured. When a urine is used as a solution to be detected, it is particularly useful to select one acid from the group consisting of potassium hydrogen phthalate, acetic acid, citric acid and ascorbic as an acid to be mixed in the reagent and/or the solution to be detected, because these acids are easy to give an appropriate buffer capacity, low cost, easy to handle, and moreover, reduce the possibility of inducing the precipitation of a phosphate, a carbonate or the like and thus are highly practicable.

According to the method for measuring a protein concentration in accordance with the present invention, it is possible to determine a protein concentration contained in urine and other body fluids such as cerebrospinal fluid, blood serum, plasma and saliva, food products such as a dairy product, liquor and vinegar, industrial fluids such as a nutrient solution, a fluid used in artificial dialysis and its waste fluid and the like.

It is also possible to determine a protein concentration and that of any optical active substance other than protein such as glucose at the same time by measuring an angle of rotation of a solution to be detected, followed by mixing of the reagent in the solution to be detected to measure the protein concentration thereof.

That is, the present invention also relates to a method for measuring a concentration of a solution comprising the steps of measuring intensities of at least a transmitted light or a scattered light of a solution to be detected before and after mixing therein one reagent selected from the group consisting of tannin, tannic acid and m-galloyl gallic acid, and measuring an angle of rotation of the solution to be detected before mixing therein the reagent, wherein a protein concentration in the solution to be detected is determined based on the intensities of at least the transmitted light or the scattered light and a concentration of any optical active substance other than protein in the solution to be detected is determined from the protein concentration and the angle of rotation.

As such, the present invention is effective especially in measuring and testing a urine protein concentration and a urine sugar value using a urine as a solution to be detected because it improves reliability and accuracy of the testing and substantially simplifies the steps thereof.

Further, the present invention relates to a reagent for measuring a protein concentration to be used in a method for measuring a protein concentration in which a reagent is mixed in a solution to be detected and a protein concentration is determined from the resulting turbidity, wherein the reagent contains at least one selected from the group consisting of tannin, tannic acid and m-galloyl gallic acid.

As described above, it is preferable that the reagent regulates a pH of the solution to be detected to 1.5 to 5.8 and contains at least one acid selected from the group consisting of potassium hydrogen phthalate, acetic acid, citric acid and ascorbic acid as a pH controlling agent.

Therefore, the reagent is preferably used in the state of an aqueous solution dissolved in water. A concentration of the reagent in the aqueous solution is preferably 250 g/dl or lower.

Further, it is preferable that the concentration of the pH controlling agent be set at the highest possible level as long as the pH controlling agent does not deposit in a temperature range operable for the reagent.

In the following paragraphs, preferred embodiments of the present invention will be described with referred to drawings. However, the present invention is not limited thereto.

Embodiment 1

A detailed description will be made on an example with reference to FIG. 1 in which an aqueous tannin solution with a concentration of 1 g/dl and a solution to be detected were mixed at a volume ratio of 1:1 to coagulate the protein thereby opacifying the solution, the scattered light intensity of the solution to be detected was measured, and the protein concentration was determined from the intensity.

Figure 2:
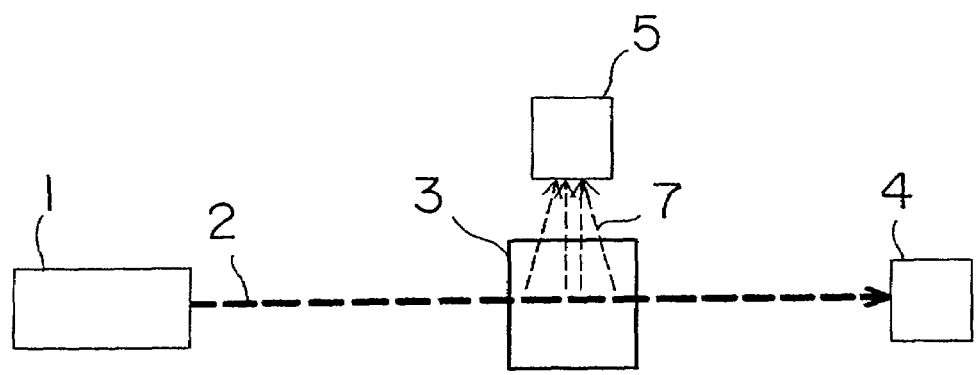
FIG. 2 is a plan view of the same apparatus.

FIG. 1 is a side view schematically showing the configuration of an apparatus used in a method for measuring a protein concentration in accordance with the present invention. FIG. 2 is a plan view showing the optical system of the same apparatus. In these figures, a reference numeral 1 denotes a semiconductor laser module as a light source, which projects a substantially parallel light 2 having a wavelength of 780 nm, an intensity of 3.0 mW and a beam diameter of 2.0 mm. A sample cell 3 is a rectangular container made of glass with the base thereof 10×10 mm, and a height of 50 mm having an opening open upwards, the side thereof being transparent optical window. The sample cell 3 is capable of irradiating the substantially parallel light 2 on a solution to be detected held therein while taking a scattered light 7 outside. The transmitted light and the scattered light are detected by a photosensor 4 for detecting a light which has transmitted the solution and a photosensor 5 for the scattered light 7 which has arisen during propagation of the light in the solution, respectively. A computer 6 controls the light source 1 and analyzes output signals from the photosensors 4 and 5.

The steps of measuring a protein concentration using an aqueous protein solution as a solution to be detected were conducted with the measuring apparatus described in FIG. 1. It should be noted that the following operations were carried out in a room having a temperature of about 40° C. and each of the temperature of a solution to be detected, a reagent and a measuring apparatus was about 40° C.

First, 1 ml each of a solution to be detected and an aqueous tannin solution with a concentration of 1 g/dl was poured in a beaker, followed by stirring. Next, the mixed solution thus obtained was introduced into the sample cell 3, whereupon the computer 6 operated the light source 1 and at the same time measured output signals from photosensors 4 and 5.

When the aqueous tannin solution reagent was mixed in the solution to be detected, the protein components coagulated to opacify the solution to be detected, thereby decreasing the intensity of the transmitted light and increasing that of the scattered light. By analyzing each of the output signals from the photosensors 4 and 5 at this time, the protein concentration was determined.

Figure 3:
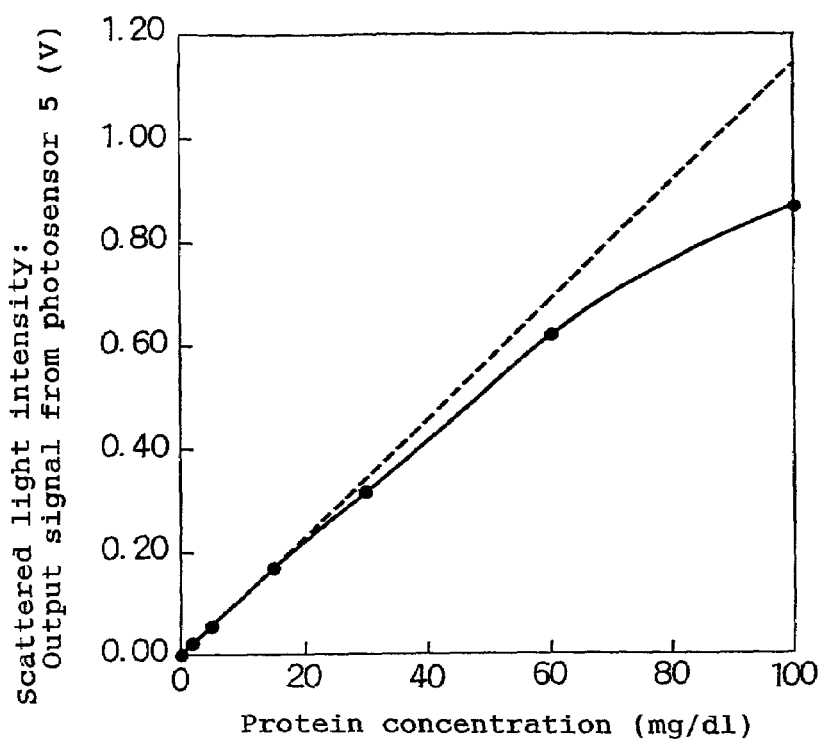
FIG. 3 is a graph showing the relation between the protein concentration in a solution to be detected and the scattered light intensity.
Figure 4:
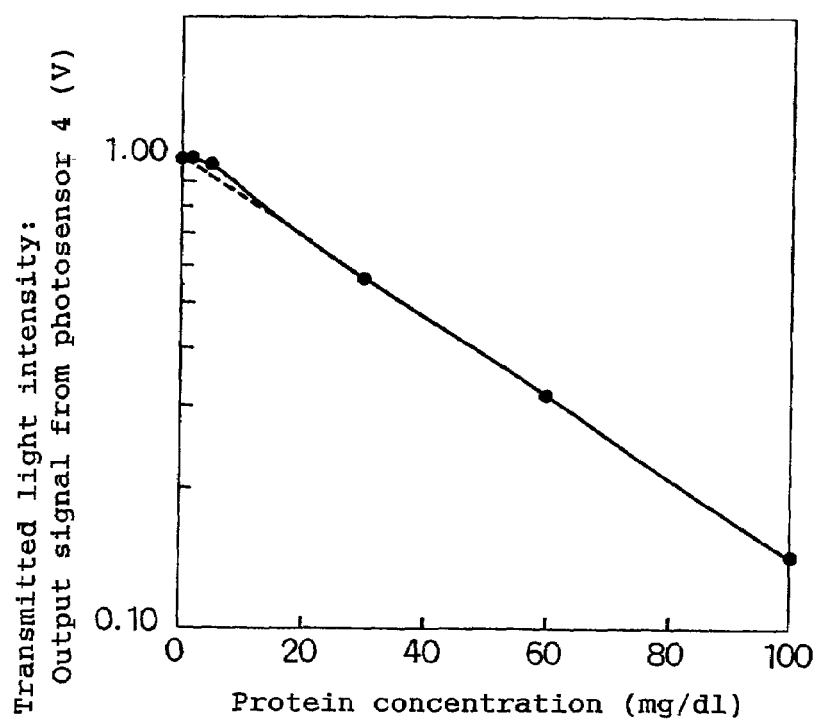
FIG. 4 is a graph showing the relation between the protein concentration in a solution to be detected and the transmitted light intensity.

Aqueous protein (serum albumin) solutions with respective concentrations of 0, 2, 5, 15, 30, 60 and 100 mg/dl were prepared. The intensities of the scattered light and the transmitted light, i.e., the output signals from the photosensors 4 and 5 were measured using these solutions with the method described above. Each of the results was plotted in FIG. 3 and FIG. 4, respectively. In FIG. 3, the abscissa denoted the protein concentration, and the ordinate denoted the scattered light intensity (the output signal from the photosensor 5). In FIG. 4, the abscissa denoted the protein concentration, and the ordinate denoted the transmitted light intensity (the output signal from the photosensor 4). It should be noted that all of the solutions used here were as transparent as water and the intensities of the transmitted light and the scattered light were the same as those of water before being mixed with the aqueous tannin solution reagent. In addition, in the case of the solution to be detected with a concentration of 0, that is, water, no change was observed in the intensity of the transmitted light and the scattered light after mixing of the aqueous tannin solution reagent, and it was substantially transparent.

In FIG. 3, each of the measured values was smoothly connected by a solid line, and the measured values in the protein concentration range of 0 to 15 mg/dl, where the scattered light intensity changed linearly to the protein concentration, were connected by a dotted line and this line was extended. As was evident from those lines, the solid and dotted lines coincided until the protein concentration reached approximately 15 mg/dl, and therefore the scattered light intensity was in proportion to the protein concentration. However, as the protein concentration became higher, the measured value gradually became lower than the corresponding value, which was in proportion to the protein concentration. The reason was considered as follows. When the protein concentration became higher, so did the probability that the light would be scattered. This increased the probability that the light would be scattered again while the scattered light propagated from the point, where it had arisen, to the outside of the sample cell, thereby decreasing the probability that the scattered light would reach the photosensor 5. Therefore, when calculating a protein concentration from the change in the scattered light intensity, the concentration could be more accurately determined in a low concentration range (about 15 mg/dl or lower) where the linearity was secured.

In FIG. 4, the abscissa denoted the protein concentration, and the ordinate (shown in logarithm) denoted the transmitted light intensity. Each of the measured values was smoothly connected by a solid line, and the measured value in the protein concentration range of 15 to 100 mg/dl, where the logarithm of the transmitted light intensity changed linearly to the protein concentration, were connected by a dotted line and this line was extended. As shown in FIG. 4, when the protein concentration was low, such as 2 and 5 mg/dl, the measured value might not be on the dotted line. The reason was considered that the output signal was more vulnerable to influences of various noises because the change in the transmitted light was too small compared with the total output signal (=1.0 V) in the case where a solution to be detected without turbidity was used. From this, it was confirmed that, when calculating a protein concentration from the change in the transmitted light intensity, the solution to be detected was preferably in a high concentration range (about 15 mg/dl or higher) to avoid the influences of the various noises.

Therefore, it was preferable that FIGS. 3 and 4 obtained as above were used as standard calibration (analytical) lines for a low concentration range and a high concentration range, respectively. Although FIGS. 3 and 4 showed examples in which each of the temperature of the solution to be detected and the reagent, and the ambient temperature were 40° C., it was possible to conduct the measurements with a temperature ranging from 0 to 50° C. Therefore, unlike the method using trichloroacetic acid as a reagent, the method in accordance with the present invention enables measurement to be conducted with a temperature of 25° C. or higher, and could be used at a possible ambient temperature at home.

As described above, a protein concentration in a solution to be detected could be determined by mixing an aqueous tannin solution reagent in the solution to be detected to measure the intensities of the transmitted light and the scattered light thereof.

Further, by measuring both of the intensities to determine a concentration of a solution to be detected in a low concentration range from the scattered light intensity, and that in a high concentration range from the intensity of the transmitted light, an accurately measurable concentration range of the solution to be detected, that is, a dynamic range, could be substantially expanded. This eliminated conventionally needed steps such as dilution of a solution to be detected in a high concentration range, thereby greatly improving the practical effects for higher accuracy, efficiency and labor saving of the measurement and the test.

In this embodiment, the concentration of the aqueous tannin solution reagent was 1 g/dl. In this case, the concentration of the reagent after being mixed in the solution to be detected was 0.5 g/dl because the mixing ratio of the reagent to the solution to be detected was 1:1. However, a protein concentration could be measured with any other concentration of the reagent after the mixing in the range of $5 \times 10^{-3}$ to 5 g/dl by forming a calibration line corresponding to the tannin concentration after mixing of the reagent. When the tannin concentration was lower than the above range, there were cases where the protein did not coagulate, so that it was difficult to conduct a stable measurement. When the tannin concentration was higher than the above range, there were cases where the coagulated protein rapidly precipitated to cause a nonuniform turbidity, preventing the solution to be detected from opacifying corresponding to the concentration around the region where the substantially parallel light 2 passed, so that it was difficult to conduct a stable measurement. Therefore, it was practically preferable that measurement be conducted within the above concentration range.

Embodiment 2

Figure 5:
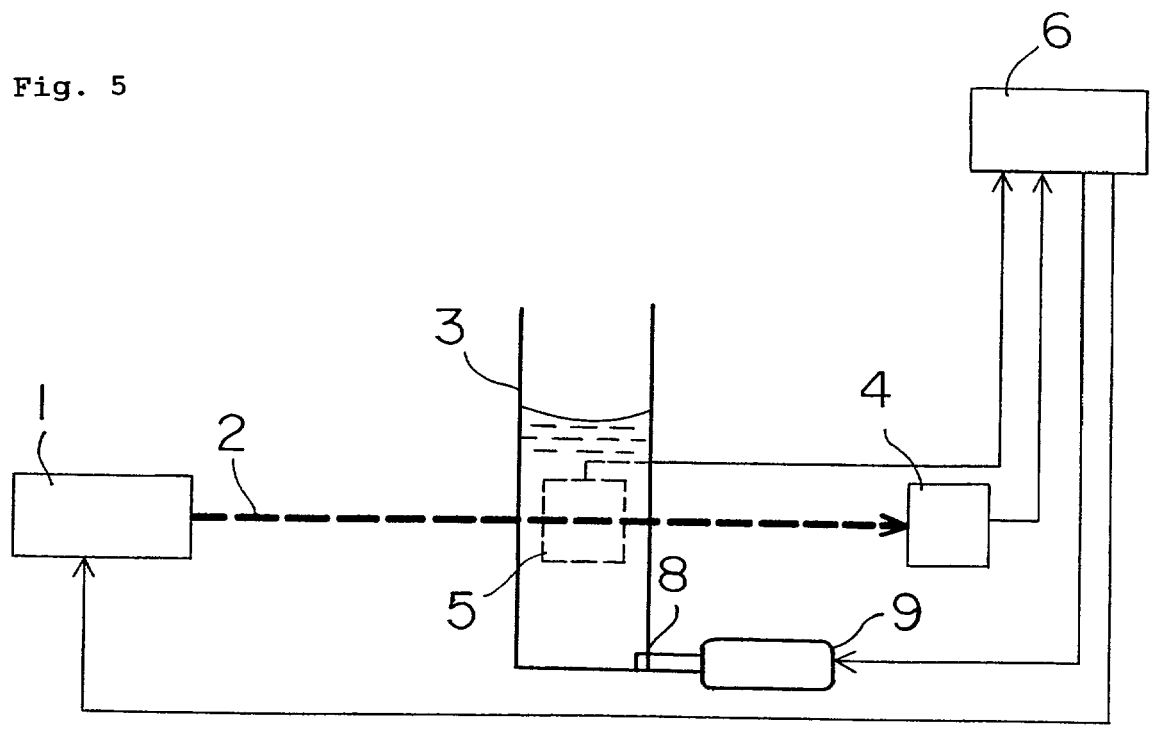
FIG. 5 is a side view schematically showing the configuration of a measurement apparatus used in another embodiment of the present invention.
Figure 6:
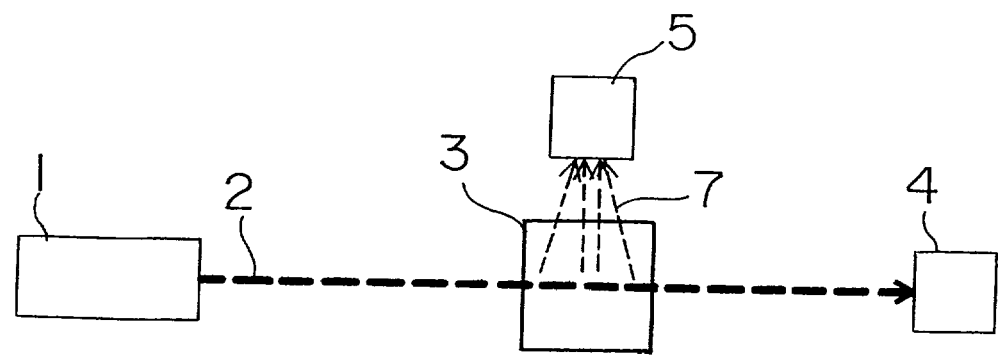
FIG. 6 is a plan view of the same apparatus.

FIG. 5 is a side view schematically showing the configuration of an apparatus used in a method for measuring a protein concentration in accordance with the present invention. FIG. 6 is a plan view of the optical system of the same apparatus. In these figures, reference numerals 1 to 7 denote the same components indicated by the corresponding reference numerals in FIGS. 1 and 2, and the configurations thereof are also the same as those in FIGS. 1 and 2. At the bottom of the sample cell 3, an inlet 8 for a reagent was provided, through which a reagent of a predetermined amount was mixed in a solution to be detected in the sample cell 3 with a pipette 9. The computer 6 controlled the light source 1 and the pipette 9, while analyzing output signals from the photosensors 4 and 5.

In this embodiment, an aqueous tannic acid solution was mixed in a solution to be detected to coagulate protein thereby opacifying the solution to be detected, and the protein concentration was determined based on the change in turbidity after mixing of the aqueous tannic acid solution. Specifically, an aqueous tannic acid solution reagent with a concentration of $3 \times 10^{-4}$ M ($\approx 0.05$ g/dl) and the solution to be detected were mixed at a volume ratio of 1 to 9 to measure the intensities of the transmitted light and/or the scattered light before and after mixing of the reagent, and the protein concentration in the solution to be detected was determined from the intensities. Herein, the concentration of tannic acid in the solution to be detected after mixing of the reagent was $3 \times 10^{-5}$ M ($\approx 5 \times 10^{-3}$ g/dl). As in Embodiment 1, the following operations were conducted in a room having a temperature of about 40° C., and each of the temperature of the solution to be detected, the reagent and the measuring apparatus was about 40° C.

A protein concentration was tested by using a urine as a solution to be detected with the above measuring apparatus in the followings.

First, 1.8 ml of a solution to be detected was introduced into the sample cell 3, whereupon the computer 6 operated the light source 1 and at the same time started to monitor the output signals from the photosensors 4 and 5. Next, the computer 6 controlled the pipette 9 so as to mix 0.2 ml of an aqueous tannic acid solution reagent in the sample cell 3 through the inlet 8. Upon mixing of the tannic acid reagent in the solution to be detected, the protein components of the solution to be detected coagulated to opacify the solution, thereby decreasing the intensity of the transmitted light and increasing that of the scattered light. The protein concentration was determined by analyzing each of the output signals from the photosensors 4 and 5 before and after mixing of the reagent.

Figure 7:
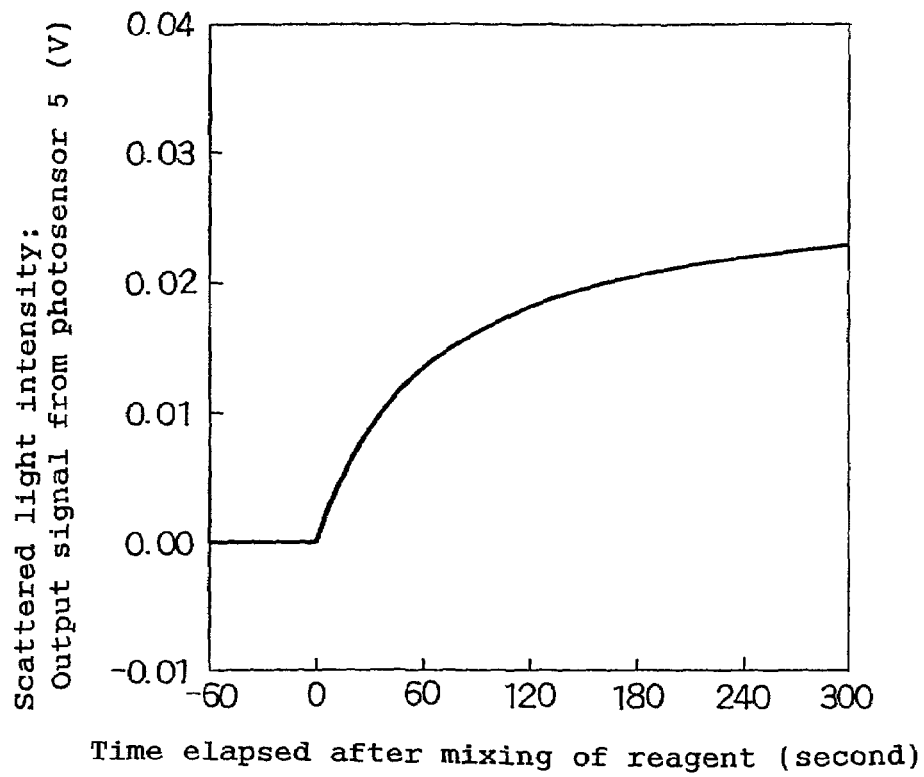
FIG. 7 is a graph showing the change in the scattered light intensity of a solution to be detected.
Figure 8:
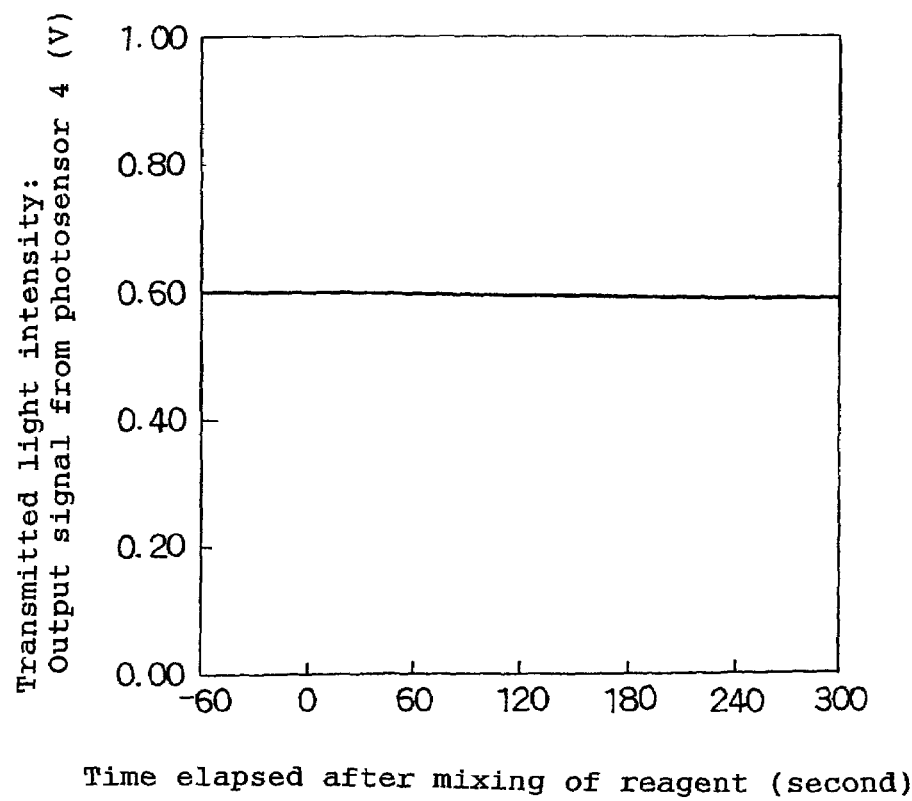
FIG. 8 is a graph showing the change in the transmitted light intensity of a solution to be detected.

The intensities of the scattered light and transmitted light, i.e., the output signals from the photosensors 4 and 5, which were measured by using a solution to be detected with a protein concentration of 5 mg/dl with the above method, were plotted in FIGS. 7 and 8, respectively. In FIGS. 7 and 8, the abscissa denoted the time elapsed (second) after mixing of the reagent, and the ordinate denoted the intensities of the lights detected by the photosensors, indicating the change in the intensities of the scattered light or the transmitted light which occurred from 60 seconds before to 300 seconds after mixing of the reagent.

Figure 9:
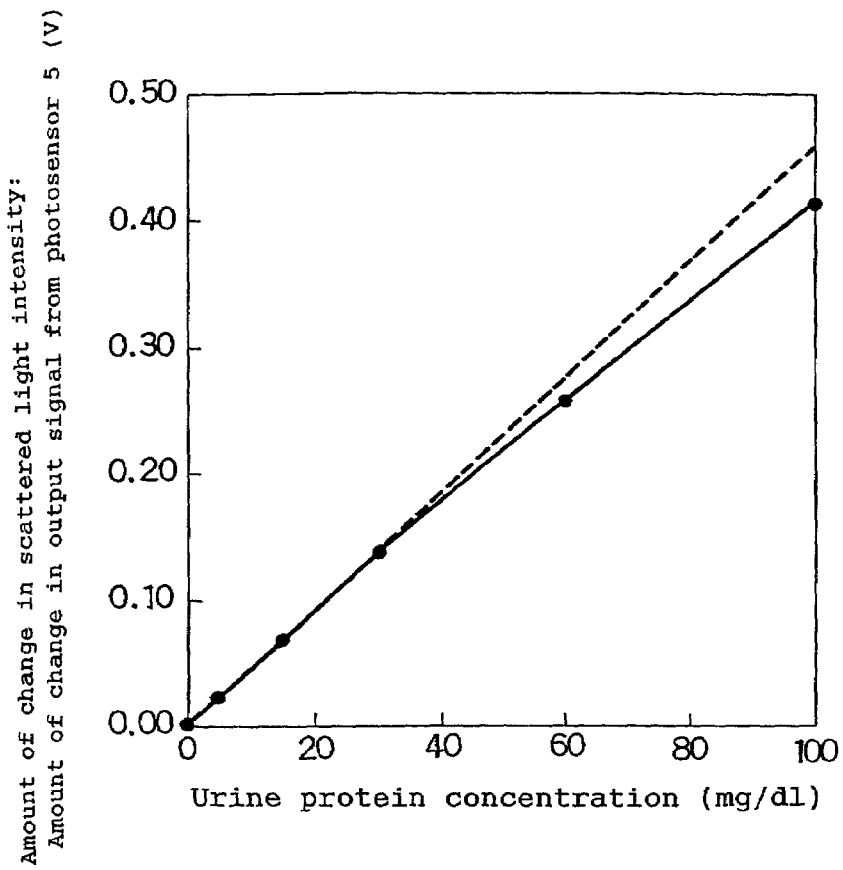
FIG. 9 is a graph showing the relation between the protein concentration in a solution to be detected and the amount of change in the transmitted light intensity.
Figure 10:
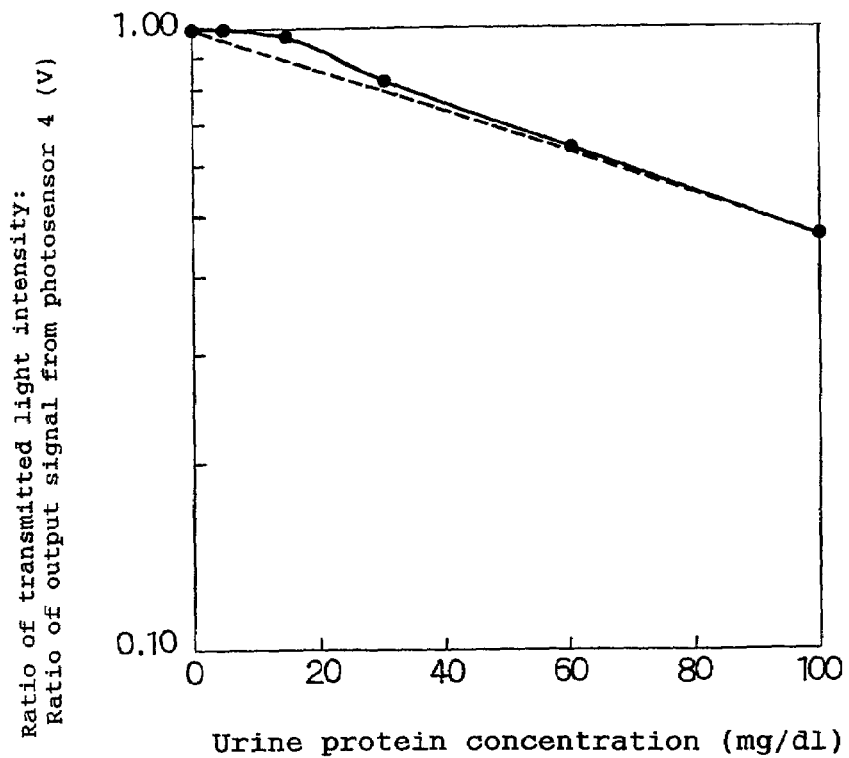
FIG. 10 is a graph showing the relation between the protein concentration in a solution to be detected and the ratio of the transmitted light intensity.

The correlation between the change in the scattered light intensity and the protein concentration, and that between the ratio of the transmitted light intensity and the protein concentration were plotted in FIGS. 9 and 10, respectively. In FIG. 9, the ordinate denoted the difference between the scattered light intensities before and 300 seconds after mixing of the reagent ((the scattered light intensity after mixing of the reagent)–(the scattered light intensity before mixing of the regent)). In FIG. 10, the ordinate denoted the ratio of the transmitted light intensity 300 seconds after mixing of the reagent to that before mixing of the reagent ((the transmitted light intensity after mixing of the reagent)/(the transmitted light intensity before mixing of the reagent)). The results of measuring urines with respective concentrations of 0, 15, 30, 60 and 100 mg/dl as a solution to be detected were plotted in FIGS. 9 and 10, in addition to that of the solution to be detected with a protein concentration of 5 mg/dl. In these cases, all of the measured solutions to be detected were optically as transparent as water, and the intensities of the transmitted light and scattered light thereof were the same as those of water, before mixing of the reagent.

In FIG. 9, each of the measured values was smoothly connected by a solid line, and the measured values in the protein concentration range of 0 to 30 mg/dl, where the amount of change in the scattered light intensity (the difference between the scattered light intensities before and after mixing of the reagent) changed linearly to the protein concentration, were connected by a dotted line and this line was extended. By using this solid line as a calibration line, the protein concentration could be obtained. Further, as was evident from those lines, the solid and dotted lines coincided until the protein concentration reached approximately 30 mg/dl, and therefore the amount of change in the scattered light intensity was in proportion to the protein concentration. However, as the protein concentration became higher, the measured value gradually became lower than the corresponding value, which was in proportion to the protein concentration. The reason was considered as follows. When the protein concentration became high, so did the probability that the light would be scattered. This increased the probability that the light would be scattered again while the scattered light propagated from the point, where it had arisen, to the outside of the sample cell, thereby decreasing the probability that the scattered light would reach the photosensor 5. Therefore, when calculating a protein concentration from the change in the scattered light intensity, the concentration could be more accurately determined in a low concentration range (about 30 mg/dl or lower) where the linearity was secured.

In FIG. 10, the abscissa denoted the protein concentration, and the ordinate (shown in logarithm) denoted the ratio of the transmitted light intensity after mixing of the reagent to that before mixing of the reagent. Each of the measured values was smoothly connected by a solid line, and the measured values in a protein concentration range of 60 to 100 mg/dl, where the logarithm of the transmitted light intensity changed linearly to the protein concentration, were connected by a dotted line and this line was extended. As shown in FIG. 10, when the protein concentration was not higher than 30 mg/dl, there were cases where the measured value was not on the dotted line. The reason was considered that the output signal was more vulnerable to influences of various noises because the change in the transmitted light was too small compared with the total output signal. From this, it was found that, when calculating a protein concentration from the transmitted light intensity, the solution to be detected was preferably in a high concentration range (about 30 mg/dl or higher) to avoid the influences of various noises.

As described above, a protein concentration in a solution to be detected could be determined by measuring the intensities of the transmitted light or the scattered light before and after mixing of the reagent. Further, by measuring both of the intensities to determine a concentration of a solution to be detected in a low concentration range from the scattered light intensity, and that in a high concentration range from the transmitted light intensity, an accurately measurable concentration range of the solution to be detected, that is, a dynamic range, could be expanded.

According to this embodiment, a protein concentration could be determined using a urine which had been opacified by precipitation of various kinds of salts. This will be described in the following.

First, a turbid urine with a protein concentration of 30 mg/dl was introduced into the sample cell 3 as a solution to be detected. Herein, the output signal from the photosensor 5 (scattered light intensity) was about 0.05 V. Since the output signal of the photosensor 5 before mixing of the reagent was 0.0 V in the case of a solution to be detected without turbidity from FIG. 7, it could be said that the difference between these output signals indicated the level of turbidity inherent in the solution to be detected of this embodiment. The protein concentration corresponding to this value was 10 to 12 mg/dl with the solid line shown in FIG. 9 as a calibration line. At this point, the reagent was mixed in the solution to be detected and the change in the output signals from the photosensors 4 and/or 5 were observed. The output signal from the photosensor 5 when 300 seconds had passed after mixing of the reagent was 0.19 V. Therefore, the difference between this signal and the output signal when 0 second had passed after mixing of the reagent was 0.14 V. The protein concentration corresponding to this difference between the output signals (0.14 V) was 30 mg/dl with the solid line shown in FIG. 9 as a calibration line. This concentration agreed with a known concentration which had been measured in advance. From this, it was confirmed that the protein concentration in the turbid solution to be detected could be accurately determined from the difference between the output signals from the photosensor 5 before and after mixing of the reagent by using the calibration line of FIG. 9, which had been obtained from the solution to be detected without turbidity.

As described above, the concentration of a solution could be accurately determined without any influence exerted by turbidity or the like by calculating the concentration of the solution from the difference between the scattered light intensities before and after mixing of the reagent.

Meanwhile, the output signal from the photosensor 4 (transmitted light intensity) before mixing of the reagent was 0.55 V. Since the output signal from the photosensor 4 before mixing of the reagent was 0.6 V in a transparent solution to be detected without turbidity as shown in FIG. 8, the difference could be attributed to the turbidity of the solution. The output signal was 0.45 V when 300 seconds had passed after mixing of the reagent, and therefore the ratio of these signals was 0.82. The protein concentration corresponding to the ratio of the output signals (0.82) was 30 mg/dl with the solid line shown in FIG. 10 as a calibration line. This concentration agreed with a known concentration, which had been measured in advance. From this, it was confirmed that the protein concentration in a turbid solution to be detected could be accurately determined by obtaining the ratio of the output signals from the photosensor 4 after mixing of the reagent to that before mixing of the reagent and converting it to a protein concentration using FIG. 10 obtained from the solution to be detected without turbidity as a calibration line.

In this embodiment, the concentration of the solution was determined from the intensities of the transmitted light and the scattered light immediately before and 300 seconds after mixing of the reagent. However, the lapse of time may be set appropriately according to the measuring apparatus, the characteristics of the solution to be detected and the tannic acid reagent such as the concentration.

Although examples were shown in FIGS. 7 to 10 in which each of the temperature of the solution to be detected and the reagent, and the ambient temperature were 40° C., it was possible to conduct measurement at a temperature ranging from 0 to 50° C. Therefore, unlike the method using trichloroacetic acid as a reagent, the method in accordance with the present invention enabled measurement to be conducted at a temperature of 25° C. or higher, and could be used at a possible ambient temperature at home.

In this embodiment, an aqueous tannic acid solution reagent with a concentration of $3 \times 10^{-4}$ ($\approx 0.05$ g/dl) and a solution to be detected were mixed at a volume ratio of 0.1 to 0.9 to regulate the tannic acid concentration in the solution to be detected to $3 \times 10^{-5}$ ($\approx 5 \times 10^{-3}$ g/dl) after mixing of the reagent. However, the protein concentration could be measured at any other concentration of the reagent after the mixing in the range of $3 \times 10^{-5}$ to $3 \times 10^{-2}$ M ($\approx 5 \times 10^{-3}$ to 5 g/dl) by forming a calibration line corresponding to the tannic acid concentration after mixing of the reagent. When the tannic acid concentration was lower than the above range, there were cases where protein did not coagulate, so that it was difficult to conduct a stable measurement. When the tannic acid concentration was higher than the above range, the coagulated protein rapidly precipitated to cause a nonuniform turbidity, preventing the solution to be detected from opacifying corresponding to the concentration around the region where the substantially parallel light 2 passed, so that it was difficult to conduct a stable measurement. Therefore, it was practically preferable that measurement be conducted within the above concentration range.

In this embodiment, the mixing ratio of the solution to be detected to the reagent was 9:1. However, even when a tannic acid concentration after mixing of the reagent was $3 \times 10^{-5}$ M ($\approx 5 \times 10^{-3}$ g/dl), which was the same as the above example, the calibration line changed if the mixing ratio was different. Therefore, it was necessary to form a calibration line corresponding to the mixing ratio. Herein, if the mixing ratio of the solution to be detected to the reagent increased, for example, to 1:1, the turbidity of the solution to be detected became low compared with the solution to be detected with the same protein concentration. Therefore, if the tannic acid concentration after the mixing of the reagent was kept constant, it was advantageous to use an aqueous tannic acid solution reagent with a high tannic acid concentration, because lowering of the mixing ratio was effective to simply improve the sensitivity of the solution to be detected to the protein concentration. Here, it was confirmed that a tannic acid concentration where neither precipitation nor denaturation occurred was not higher than 1.5 M ($\approx$250 g/dl). Therefore, it was effective to set a concentration of the aqueous tannic acid solution reagent not higher than this concentration.

Embodiment 3

In this embodiment, the presence or absence of an obstruction of measurement due to a suspending particle such as a bubble in a solution to be detected was detected by measuring output signals from the photosensors 4 and 5 and comparing the measured values using the apparatus shown in FIGS. 5 and 6 with the same method as in Embodiment 2.

When any suspending particle such as a bubble was present in a solution to be detected and entered into an optical path of the substantially parallel light 2, the substantially parallel light 2 was highly scattered, thereby obstructing an accurate measurement of intensities of the transmitted light and/or the scattered light. In this case, the transmitted light intensity substantially decreased. On the other hand, the scattered light intensity either substantially decreased or increased, depending on the angle of visibility of the photosensor 5, the location of the suspending particle such as a bubble present in the optical path and the like.

When no obstruction due to a suspending particle such as a bubble was present, there existed a certain relation between the scattered light intensity and the transmitted light intensity as shown in FIGS. 9 and 10. For example, the difference between the scattered light intensities before and after mixing of the reagent was 0.14 V, and the ratio of the transmitted light intensity after mixing of the reagent to that before mixing of the reagent was 0.82 in the case where the protein concentration of the solution to be detected was 30 mg/dl. However, when the obstruction as above was present, a value inconsistent with the above relation was measured. Therefore, the presence or absence of the above-mentioned obstruction could be detected by checking whether the protein concentration obtained from the measured value of the photosensor 4 based on the calibration line of FIG. 10 was identical with that obtained from the measured values of the photosensor 5 before and after mixing of the reagent based on the calibration line of FIG. 9.

As described above, according to this embodiment, an obstacle due to a suspending particle such as a bubble could be detected to prevent an erroneous measurement by measuring both of the intensities of the transmitted light and the scattered light before and after mixing of the aqueous tannic acid solution reagent, and comparing the intensities. This improved the reliability of a measurement and greatly contributed to a practical effect, enabling improved reliability and labor saving for measurements and tests.

Embodiment 4

In this embodiment, an angle of rotation of a solution to be detected was measured before mixing therein a reagent, an aqueous m-galloyl gallic acid solution was mixed in the solution to be detected to coagulate the protein thereby to opacify the solution to be detected, the protein concentration was measured from the change in the turbidity after mixing of the reagent, and the concentration of any optical active substance other than protein was determined from the measured values.

Figure 11:
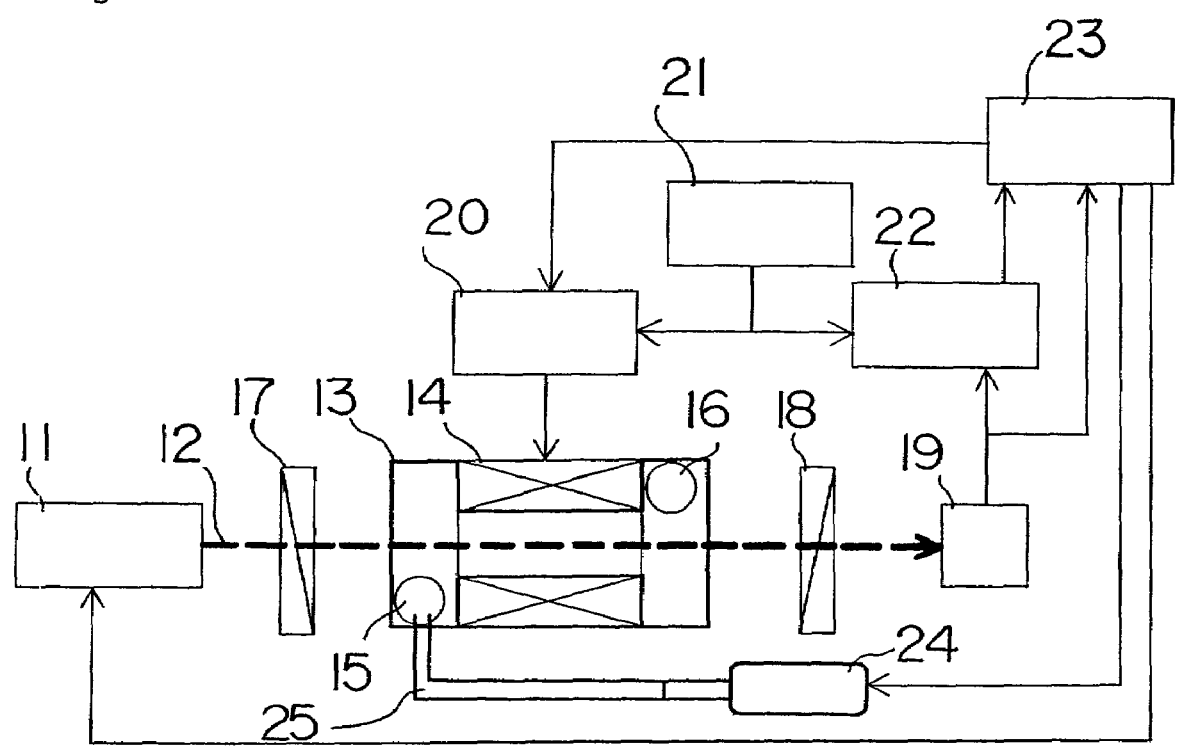
FIG. 11 is a side view schematically showing the configuration of a measurement apparatus used in still another embodiment of the present invention.

FIG. 11 is a diagram illustrating the configuration of a measuring apparatus used in this embodiment. A semiconductor laser module as a light source 11 projects a substantially parallel light 12 with a wavelength of 670 nm, an intensity of 3.0 mW and a beam diameter of 2.0 mm. A polarizer 17 transmits only a polarized light component, which is parallel to the plane of this sheet. A sample cell 13 for holding a solution to be detected is wound around by a solenoid coil 14 such that a magnetic field can be applied on the solution to be detected in the direction of propagation of the substantially parallel light 12, and has a substantial optical path length of 50 mm and a rated capacity of 5 ml. This modulates and controls the direction of polarization by modulating and controlling the current to be passed to the solenoid coil 14 using an optical Faraday effect of the solution to be detected. The basic principal of the method for measuring an angle of rotation using a Faraday effect inherent in the solution to be detected is described in Japanese Laid-Open Patent Publication No. Hei 9-145605.

The sample cell 13 is provided with an inlet 15 for a reagent and a vent hole 16 for air to enter and exit. An analyzer 18 is arranged so as to transmit only a polarized light component, which is perpendicular to the plane of this sheet. The substantially parallel light 12, which has passed through the analyzer 18 is detected at a photosensor 19. A signal generator 21 supplies a modulation signal, which modulates the current to be passed to the solenoid coil 14, to a coil driver 20. The coil driver 20 controls the current to be passed to the solenoid coil 14. A lock-in amplifier 22 makes phase-sensitive detection on the output signal from the photosensor 19 using the modulated signal of the solenoid coil 14 as a reference signal. When measuring an angle of rotation of the solution to be detected, the computer 23 supplies a control current signal to the coil driver 20 such that the output signal from the lock-in amplifier 22 becomes zero.

Specifically, after measuring an angle of rotation of the solution to be detected, an aqueous m-galloyl gallic acid solution reagent with a concentration of 7.8×10 M ($\approx$250 g/dl) and the solution to be detected were mixed at a volume ratio of 1:49 to measure the transmitted light intensities before and after mixing of the reagent. Then, the protein concentration in the solution to be detected was obtained from this intensity, and that of any optical active substance other than protein was determined from the protein concentration and the angle of rotation. Herein, the concentration of the aqueous m-galloyl gallic acid solution after mixing of the reagent was $1.6 \times 10^{-1}$ M ($\approx$5 g/dl). In the following, this will be explained in detail.

In this embodiment, a modulation current with an amplitude of 0.001 A and a frequency of 1.3 kHz was passed to the solenoid coil 14. By these, the control current signal where the output signal from the lock-in amplifier 22 became 0 was detected to calculate the angle of rotation. Here, a method was taken in which the angle of rotation was determined from the control current signal which gave a magnetic field where an angle of rotation due to protein or glucose as an optical active substance in a solution to be detected was identical with an rotating angle of a solvent water of the solution to be detected in the direction of polarization due to a Faraday effect caused by application of magnetic field.

With a pipette 24, 0.1 ml of an aqueous m-galloyl gallic acid solution was mixed in the solution to be detected in the sample cell 13 from the inlet 15 via a tube 25. The computer 23 controlled the light source 11 and the pipette 24, while analyzing an output signal from the photosensor 19.

A glucose concentration (urine sugar value) and a urine protein concentration were tested by using a urine as a solution to be detected with the above apparatus in the following.

First, the solution to be detected was introduced into the sample cell 13, whereupon the computer 23 operated the light source 11 and the coil driver 20 to measure an angle of rotation of the solution to be detected.

Figure 12:
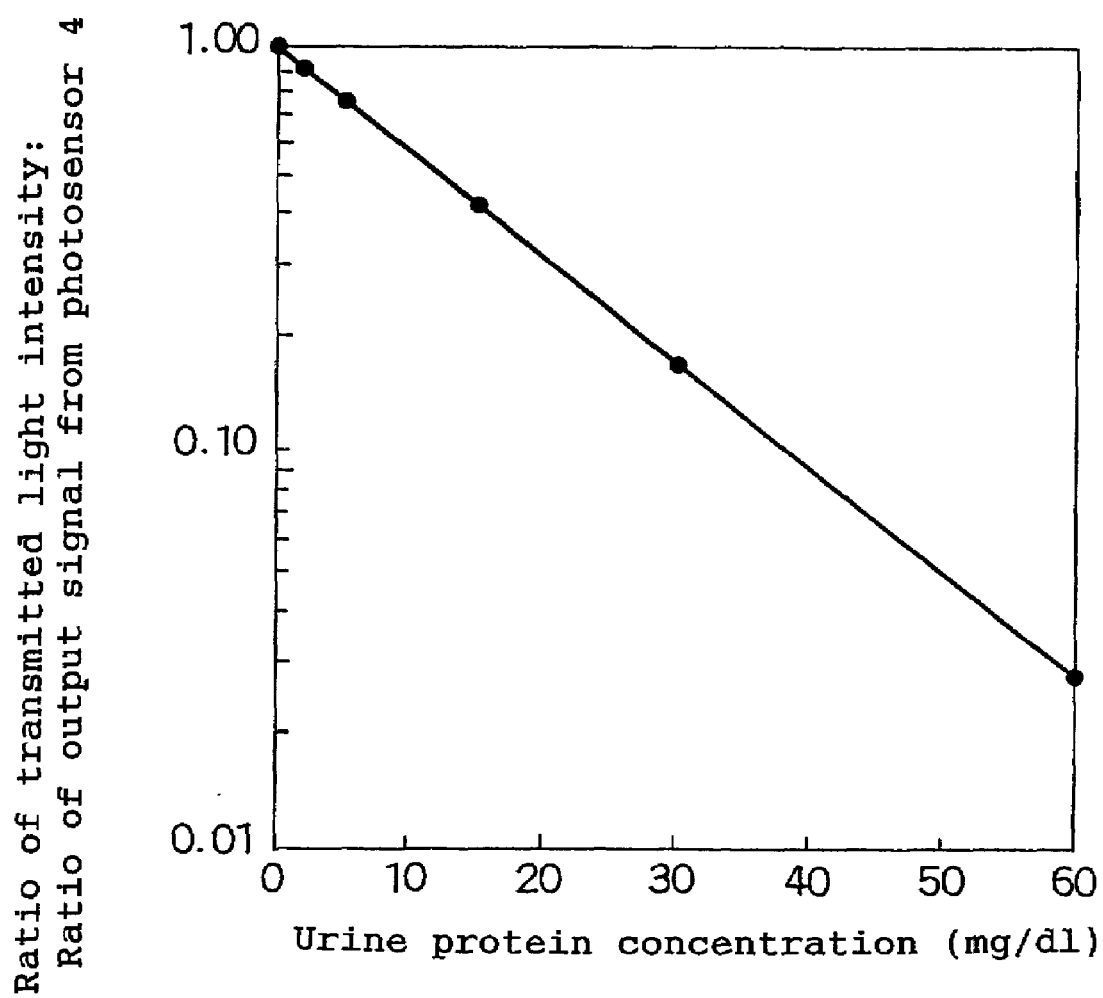
FIG. 12 is a graph showing the relation between the protein concentration in a solution to be detected and the ratio of the transmitted light intensity.

Next, the computer 23 stopped the operation of the coil driver 20 and at the same time started to monitor an output signal from the photosensor 19. Then, the computer 23 controlled the pipette 24 such that the aqueous m-galloyl gallic acid solution reagent was mixed in the solution to be detected in the sample cell 13 from the inlet 15. By assuming the change of the output signals from the photosensor 19 after mixing of the reagent as the change in the transmitted light intensity, a calibration line corresponding to FIG. 10 was formed based on the analyzed ratio of the transmitted light intensity after mixing of the reagent to that before mixing of the reagent by using urines with respective protein concentrations of 0, 2, 5, 15 and 60 mg/dl as solutions to be detected with the same method as in Embodiment 2. This calibration line is shown in FIG. 12.

In the case where a urine with a urine sugar value of 100 mg/dl and a urine protein concentration of 15 mg/dl was used as the solution to be detected as an example of the above measurement, the angle of rotation was 0.017°. The specific angle of rotation of glucose at this wavelength (670 nm) was 40° deg/cm·dl/kg. Therefore, on the assumption that all of the measured angles of rotations were due to glucose, the glucose concentration, i.e., the urine sugar value, was 85 mg/dl. Meanwhile, the protein concentration determined from FIG. 12 was 15 mg/dl because the ratio of the transmitted light intensity was 0.41. Since the specific angle of rotation of the protein was −40° deg/cm·dl/kg, the angle of rotation due to protein was −0.003°. Therefore, the true angle of rotation due to glucose was calculated at 0.02° by subtracting −0.003° from the above-mentioned 0.017° and the glucose concentration was calculated at 100 mg/dl.

From this, it was confirmed that a urine sugar value and a urine protein concentration could be accurately determined at the same time by measuring the angle of rotation of the solution to be detected before mixing of the aqueous m-galloyl gallic acid solution reagent and the ratio of the transmitted light intensity after mixing of the reagent to that before the mixing of the reagent.

As described above, according to this embodiment, a concentration of protein and that of glucose, which was another optical active substance beside protein, could be determined at the same time, and therefore the method of this embodiment was practicable especially when a solution to be detected was a urine. This will be described in the following.

When a urine protein concentration is normal, glucose is the predominant optical active substance in the urine. Therefore, the urine sugar value can be roughly examined by measuring the angle of rotation of the urine. However, a urinalysis can be conducted more accurately by determining a urine protein concentration with a measuring method other than the one based on the angle of rotation. The reason is that, when a urine protein concentration is measured based on the angle of rotation, the combination of the angle of rotation due to glucose and that due to protein are observed as the angle of rotation of the urine since protein is also an optical active substance as well as glucose. Therefore, as in this embodiment, a urine sugar value and a urine protein concentration can be accurately determined by obtaining the protein concentration from the change in the optical characteristics after mixing of the reagent, besides measuring the angle of rotation, and correcting the measured angle of rotation based on the protein concentration thus measured.

Incidentally, if the reagent was mixed in the solution to be detected before measuring the angle of rotation, the protein component coagulated, thereby preventing the light from transmitting through the solution to be detected, or causing protein to denature to change the angle of rotation. Thus, it was not possible to determine the urine sugar value and the urine protein concentration accurately.

In this embodiment, an angle of rotation and a transmitted light intensity were measured using a light with a wavelength of 670 nm. In general, the specific angle of rotation of a substance increases with the decrease of the wavelength until the wavelength reaches the one where the absorbance inherent in the substance (around 180 nm, in a case of glucose) begins. Moreover, turbidity due to the coagulation of protein increases with the decrease of the wavelength. Therefore, in terms of the sensitivity, it is more advantageous that the angle of rotation, the intensities of the scattered light and transmitted light are measured using a light with a shorter wavelength. However, when a solution to be detected is a urine, a light with a wavelength of 500 nm or shorter is absorbed by a dye contained in urine such as urochrome. For this reason, an accuracy of measurement sometimes deteriorated when conducting the measurement with a light having a wavelength of 500 nm or shorter. Therefore, it was practicable that the measurement was conducted using a light with a wavelength of 500 nm or longer.

In this embodiment, the mixing ratio of the solution to be detected to the reagent was 49:1. However, even when a concentration of m-galloyl gallic acid after mixing of the reagent was $1.6 \times 10^{-1}$ M ($\approx 5$ g/dl), which was the same as the above example, the calibration line changed if the mixing ratio was different. Therefore, it was necessary to form a calibration line corresponding to the mixing ratio. Herein, as the mixing ratio of the solution to be detected and the reagent increased, for example, to 1:1, the turbidity to the solution to be detected with the same concentration decreased. Therefore, if the tannic acid concentration after the mixing of the reagent was kept constant, it was advantageous to use an aqueous m-galloyl gallic acid solution reagent with a high m-galloyl gallic acid concentration, because lowering of the mixing ratio was effective in order to simply improve the sensitivity of the solution to be detected to the protein concentration. Here, it was confirmed that the concentration of m-galloyl gallic acid where neither precipitation nor denaturation occurred was 7.8 M ($\approx 250$ g/dl) or lower. Therefore, it was effective to set a concentration of the aqueous m-galloyl gallic acid solution reagent not higher than this concentration.

Embodiment 5

In this embodiment, an aqueous tannin-citric acid solution with a tannin concentration of 1 g/dl and a citric acid concentration of 20 g/dl was used as a reagent. The pH of the reagent was approximately 1.4 to 1.5.

The above reagent and a solution to be detected were mixed at a volume ratio of 1:1 to coagulate protein thereby to opacify the solution, the intensity of the scattered light of the solution was measured, and the protein concentration was determined from the intensity.

The steps of measuring a protein concentration using an aqueous protein solution as a solution to be detected were conducted with the measuring apparatus described in FIG. 1. It should be noted that the following operations were carried out in a room having a temperature of about 40° C. and each of the temperature of a solution to be detected, a reagent and a measuring apparatus was about 40° C.

First, 1 ml each of a solution to be detected and an aqueous tannin-citric acid solution with a tannin concentration of 1 g/dl and a citric acid concentration of 20 g/dl were poured in a beaker, followed by stirring. Next, the mixed solution thus obtained was introduced into the sample cell 3, whereupon the computer 6 operated the light source 1 and at the same time analyzed output signals from photosensors 4 and 5.

Upon mixing of the aqueous tannin-citric acid solution reagent in the solution to be detected, the protein components coagulated to opacify the solution, thereby decreasing the intensity of the transmitted light and increasing that of the scattered light. The protein concentration was determined by analyzing each of the output signals from the photosensors 4 and 5 at this time.

Figure 13:
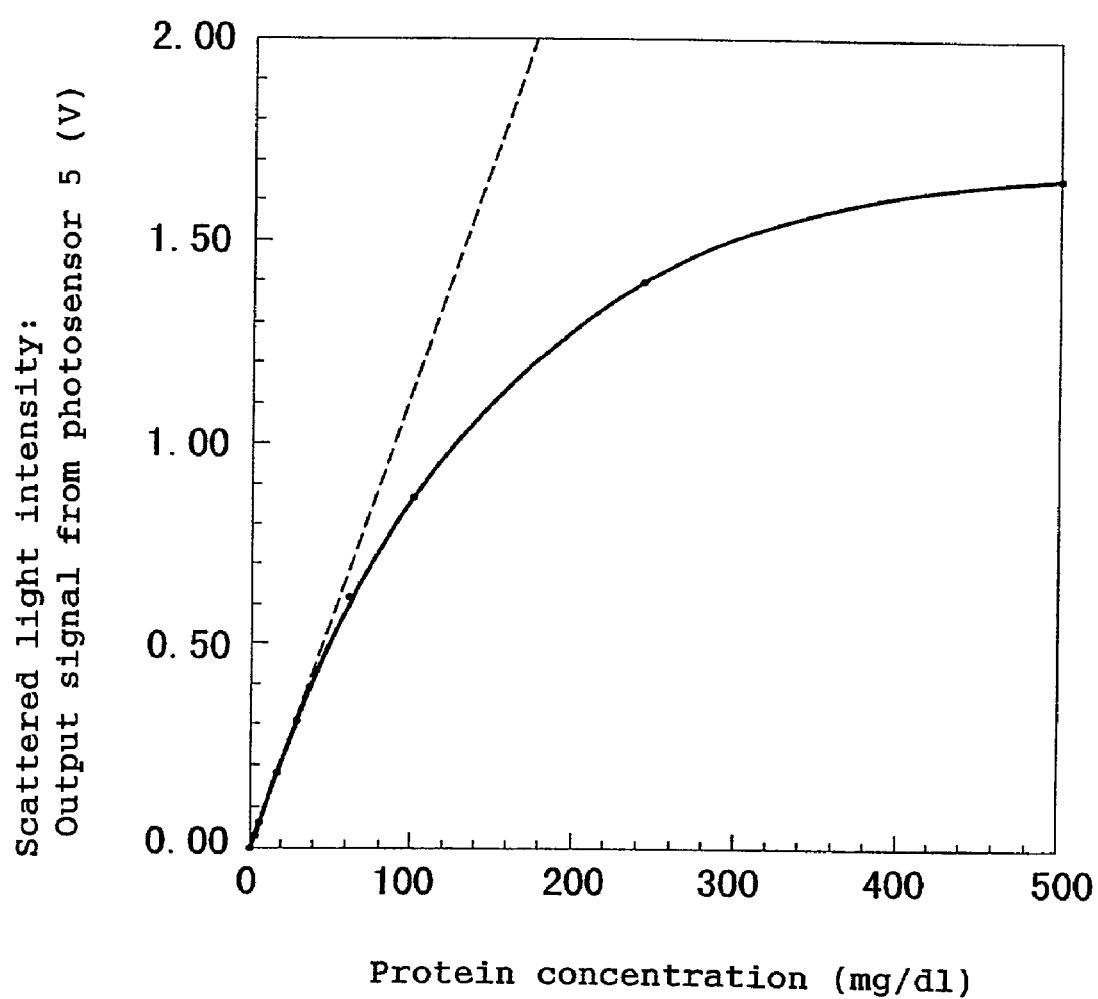
FIG. 13 is a graph showing the relation between the protein concentration in the solution to be detected and the scattered light intensity.
Figure 14:
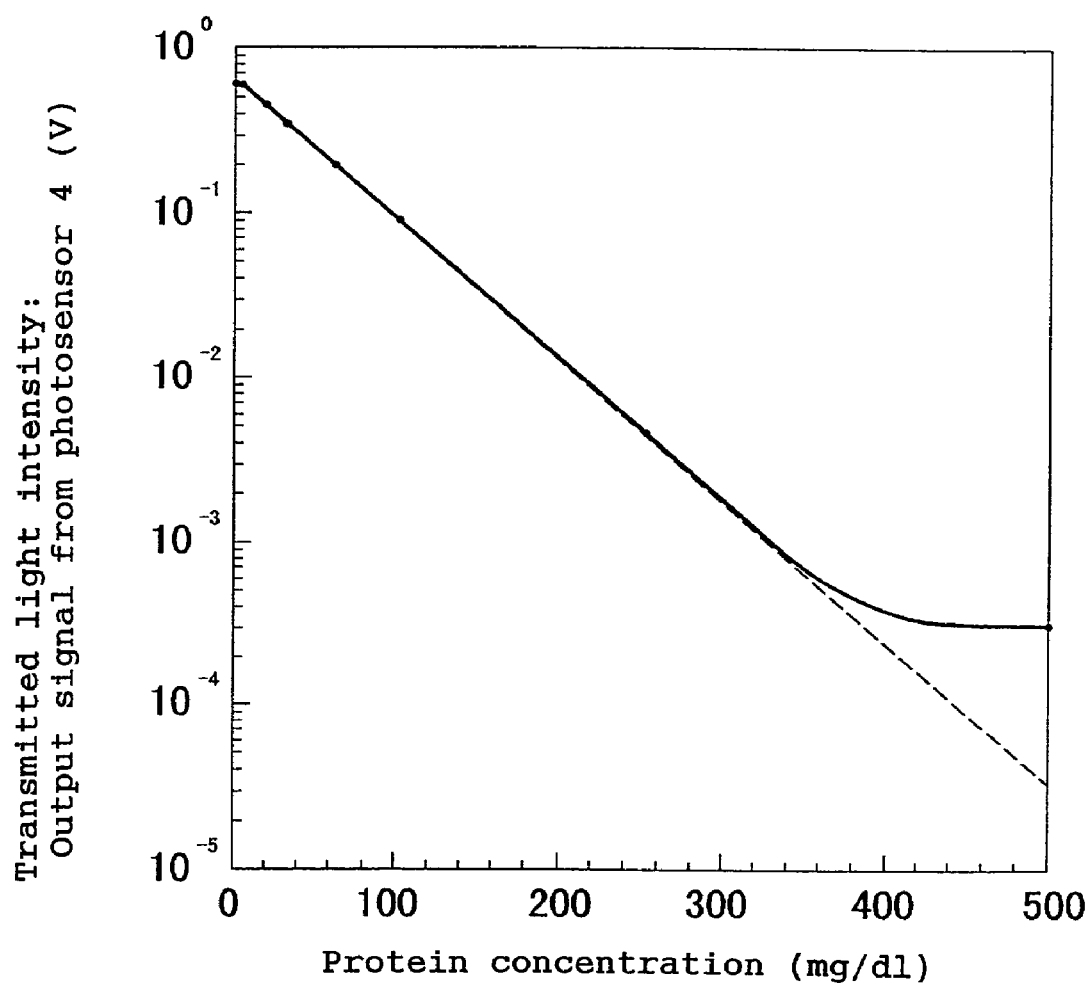
FIG. 14 is a graph showing the relation between the protein concentration in a solution to be detected and the transmitted light intensity.

Aqueous protein solutions (serum albumin) with respective concentrations of 0, 2, 5, 15, 30, 60, 100, 250 and 500 mg/dl were prepared. The intensities of the scattered light and the transmitted light, i.e., the output signals from the photosensors 5 and 4, were measured using these solutions with the method described above. Each of the results was plotted in FIG. 13 and FIG. 14, respectively. In FIG. 13, the abscissa denoted the protein concentration, and the ordinate denoted the scattered light intensity (output signal from photosensor 5). In FIG. 14, the abscissa denoted the protein concentration, and the ordinate denoted the transmitted light intensity (output signal from photosensor 4). It should be noted that all of these solutions used here were as transparent as water and the intensities of the transmitted light and the scattered light thereof were the same as those of water before mixing therein the above reagent. In addition, in the case of the solution to be detected with a concentration of 0, that is, water, no change was observed in the intensities of the transmitted light and the scattered light after mixing of the reagent, and the solution to be detected was substantially transparent.

In FIG. 13, each of the measured values was smoothly connected by a solid line, and the measured values in a protein concentration range of 0 to 15 mg/dl, where the scattered light intensity changed linearly to the protein concentration, were connected by a dotted line and this line was extended. As was evident from those lines, the solid and dotted lines coincided until the protein concentration reached approximately 15 mg/dl, indicating that the scattered light intensity was in proportion to the protein concentration. However, as the protein concentration became higher, the measured value gradually became lower than the corresponding value which was in proportion to the protein concentration. The reason was considered as follows. When the protein concentration became higher, so did the probability that the light would be scattered. This increased the probability that the light would be scattered again while the scattered light propagated from the point, where it had arisen, to the outside of the sample cell, so that the probability that the scattered light would reach the photosensor 5 became low. Therefore, when calculating a protein concentration from the change in the scattered light intensity, the concentration could be more accurately determined in a solution to be detected in the low concentration range (about 15 mg/dl or lower) where the linearity was secured. A protein concentration in a middle and high concentration ranges (above 15 mg/dl or higher), which did not agree with the linearity, could be determined by using a calibration line shown by the solid line.

It was also confirmed that a concentration in the range of up to 500 mg/dl could be measured directly because the solution to be detected did not become completely saturated.

Herein, when citric acid was not mixed in the aqueous tannin solution, there was a case where the scattered light intensity (output signal from photosensor 5) at a concentration of 500 mg/dl became 1.0 V or lower, resulting in an erroneous operation in which the concentration was assumed as about 120 mg/dl or lower.

However, as shown in this embodiment, by using a reagent prepared by mixing citric acid in an aqueous tannin solution, it was possible to cause turbidity corresponding to the concentration even in a case of the solution to be detected with a high concentration such as 500 mg/dl.

In FIG. 14, the abscissa denoted the protein concentration, and the ordinate (shown in logarithm) denoted the transmitted light intensity. Each of the measured values was smoothly connected by a solid line, and the measured value in a protein concentration range of 15 to 100 mg/dl, where the logarithm of the transmitted light intensity changed linearly to the protein concentration, were connected by a dotted line and this line was extended. As shown in FIG. 4, when the protein concentration of a solution to be detected was low, such as 2 and 5 mg/dl, there were cases where the measured value was not on the dotted line. The reason was considered that the output signal was more vulnerable to influences of various noises because the change in the transmitted light was too small compared with the total output signal (=1.0 V) in the case where a solution to be detected without turbidity was used. From this, it was confirmed that, when calculating a protein concentration from the transmitted light intensity, the solution to be detected was preferably in a high concentration range (about 15 to 100 mg/dl) to avoid the influences of various noises.

However, when the concentration was in the high concentration range (about 100 mg/dl or higher), the solid line was gradually separated from the linear dotted line. The reason was considered as follows. When turbidity became extremely high, the following phenomena occurred as a result of scatterings such as a multiple scattering: a light which had propagated a plurality of paths reached the photosensor 4; the output signal from the photosensor 4 decreased (about $10^{-4}$ V) to become more vulnerable to the influence of various kinds of noises. Therefore, when determining a protein concentration from the transmitted light intensity, the concentration could be more accurately determined in the high concentration range (from about 15 to 100 mg/dl) where the linearity was secured. A protein concentration in a middle and high concentration ranges (above 100 mg/dl), which did not secure the linearity, could be determined by using a calibration line shown by the solid line. It was also confirmed that a protein concentration in the range of up to 500 mg/dl could be measured directly, because the solution to be detected did not become completely saturated.

Herein, when citric acid was not mixed in the aqueous tannin solution, there were cases where the transmitted light intensity (output signal from photosensor 4) at a protein concentration of 500 mg/dl became 0.05 V or higher, resulting in an erroneous operation in which the concentration was assumed as about 120 mg/dl or lower. However, by using a reagent prepared by mixing citric acid in an aqueous tannin solution, it was possible to cause turbidity corresponding to the concentration even in the case of the solution to be detected with a high concentration such as 500 mg/dl as shown in this embodiment. Therefore, a high accuracy could be ensured by using the dotted lines of FIGS. 3 and 4 thus obtained to calculate the concentrations in a high concentration range and a low concentration range, respectively.

Although, in FIGS. 13 and 14, examples were shown in which each of the temperature of the solution to be detected and the reagent, and the ambient temperature were 40° C., it was possible to conduct the measurements with a temperature ranging from 0 to 50° C. In this case, however, it was preferable to use dotted lines and solid lines corresponding to those in FIGS. 13 and 14 for the respective temperatures. Therefore, unlike the method using trichloroacetic acid as a reagent, the method in accordance with the present invention enabled measurements to be conducted at a temperature of 25° C. or higher, and could be used at a possible ambient temperature at home.

As described above, a protein concentration in a solution to be detected could be determined by mixing an aqueous tannin-citric acid solution reagent in the solution to be detected and measuring intensities of the transmitted light and the scattered light thereof.

Further, by measuring both of the intensities to determine a concentration in a solution to be detected in a low concentration range from the scattered light intensity, and that in a middle concentration range from the transmitted light intensity, an accurately measurable concentration range of the solution to be detected, that is, a dynamic range, could be substantially expanded. This eliminated conventionally needed steps such as dilution of a solution to be detected in a high concentration range, thereby greatly improving the practical effects for higher accuracy, efficiency and labor saving of the measurement and the test.

The pHs of mixed solutions prepared by mixing aqueous protein (serum albumin) solutions to be detected with respective concentration of 0, 2, 5, 15, 30, 60, 100, 250 and 500 mg/dl and the above aqueous tannin-citric acid solution reagent were in the range of 1.5 to 1.9. In this embodiment, the reagent used was prepared by adding citric acid in the aqueous tannin solution. However, the similar effect could be obtained by using any acid capable of regulating the pH of the solution after mixing the solution to be detected and the reagent to 1.5 to 5.8. The similar effect could also be obtained by adding an acid in the solution to be detected to regulate the pH of the solution after mixing of the reagent to 1.5 to 5.8. Herein, when the kind or the amount of the acid to be mixed in the solution to be detected and/or in the reagent was different, different calibration lines (corresponding to the dotted lines and solid lines of FIGS. 13 and 14) were obtained. Therefore, it was necessary to form different calibration lines (corresponding to the dotted lines and solid lines of FIGS. 13 and 14). When the pH of the solution to be detected was not in the above-mentioned range, there were cases where the protein did not coagulate at all, so that it was impossible to conduct a stable measurement. Thus, it was practically preferable to conduct the measurement within the above pH range.

In this embodiment, the tannin concentration in the aqueous tannin-citric solution reagent was 1 g/dl. In this case, the concentration of the reagent after being mixed in the solution to be detected was 0.5 g/dl because the mixing ratio of the reagent to the solution to be detected was 1:1. However, in the case where the concentration of the reagent was different from the above value, a protein concentration could be measured by forming a calibration line (corresponding to the dotted lines and the solid lines of FIGS. 13 and 14) according to the tannin concentration after mixing of the reagent in the solution to be detected so long as it was in the range of $5 \times 10^{-3}$ to 5 g/dl. When the tannin concentration was lower than the above range, there were cases where protein did not coagulate, so that it was difficult to conduct a stable measurement. When the tannin concentration was higher than the above range, the coagulated protein rapidly precipitated to cause a nonuniform turbidity, preventing the solution to be detected from opacifying in accordance with the concentration around the region where the substantially parallel light 2 passed, so that it was difficult to conduct a stable measurement. Therefore, it was practically preferable that measurement was conducted within the above concentration range.

In this embodiment, it was stated that, with respect to concentrations in a low concentration range (about 15 mg/dl or lower), a middle concentration range (from about 15 to 100 mg/dl) and a high concentration range (about 100 mg/dl or higher), more accurate results could be obtained by measuring a concentration in the low concentration range based on the scattered light intensity and that in the middle concentration range based on the transmitted light intensity. However, it should be noted that the respective values of the low, middle and high concentration ranges might change depending on the optical path length of the sample cell 3, the propagated distance of the scattered light 7 in the solution to be detected, the location of the optical system, the kind of the reagent or the like, and were not limited to the above values. Actually, a protein concentration of 15 mg/dl or lower could be calculated by measuring the transmitted light intensity when the optical path length of the transmitted light was set to be longer than that in this embodiment (longer than 10 mm). However, such an elongation of the optical path length reduced the output signal from the photosensor 4 (approximately $10^{-4}$ V) in the case of a high concentration range, so that it was difficult to determine the concentration. Moreover, the elongation of the optical path length inherently expanded the size of the apparatus and therefore was not practically preferable. The greatest merit obtained by the present invention was that a measurable concentration range, or a dynamic range, could be expanded by using both the scattered light intensity and the transmitted light intensity when the configuration or the size of the apparatus was under a certain restriction.

Embodiment 6

In this embodiment, an aqueous tannic acid-citric acid solution was mixed in a solution to be detected to coagulate protein thereby opacifying the solution to be detected, and the protein concentration was measured from the change in turbidity and after mixing of the aqueous tannic acid-citric acid solution. Specifically, an aqueous tannic acid-citric acid solution with a tannic acid concentration of $3 \times 10^{-4}$ M ($\approx 0.05$ g/dl) and a citric acid concentration of 5 g/dl was used as a reagent. The pH of this reagent was about 1.8 to 2.0.

More specifically, the aqueous tannic acid-citric acid solution reagent and the solution to be detected were mixed at a volume ratio of 1 to 9 to measure the intensities of the transmitted light and/or the scattered light before and after mixing of the reagent. Then, the protein concentration in the solution to be detected was determined from the intensities. Herein, the concentration of tannic acid after mixing of the reagent was $3 \times 10^{-5}$ M ($\approx 5 \times 10^{-3}$ g/dl). As in Embodiment 5, the following operations were conducted in a room having a temperature of about 40° C., and each of the temperature of the solution to be detected, the reagent and the measuring apparatus was about 40° C.

A protein concentration was tested by using a urine as a solution to be detected with the measuring apparatus shown in FIG. 5 in the following.

First, 1.8 ml of a solution to be detected was introduced into the sample cell 3, whereupon the computer 6 operated the light source 1 and at the same time started to monitor the output signals from the photosensors 4 and 5. Next, the computer 6 controlled the pipette 9 so as to mix 0.2 ml of an aqueous tannic acid-citric acid solution reagent in the sample cell 3 through the inlet 8. Upon mixing of the aqueous tannic acid-citric acid solution reagent in the solution to be detected, the protein component in the solution to be detected coagulated to opacify the solution, thereby decreasing the intensity of the transmitted light and increasing that of the scattered light. The protein concentration was determined by analyzing each of the output signals from the photosensors 4 and 5 before and after mixing of the reagent.

Figure 15:
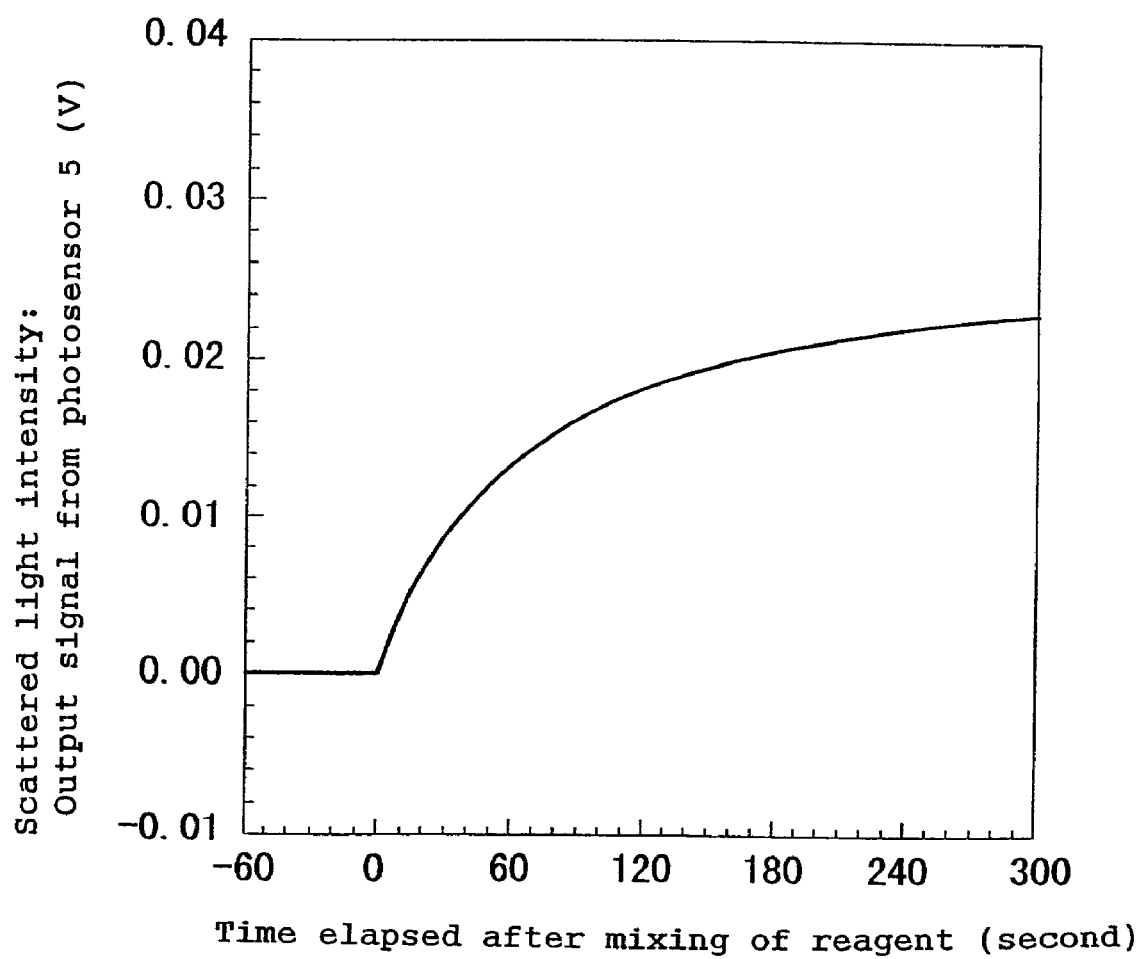
FIG. 15 is a graph showing the change in the scattered light intensity of a solution to be detected.
Figure 16:
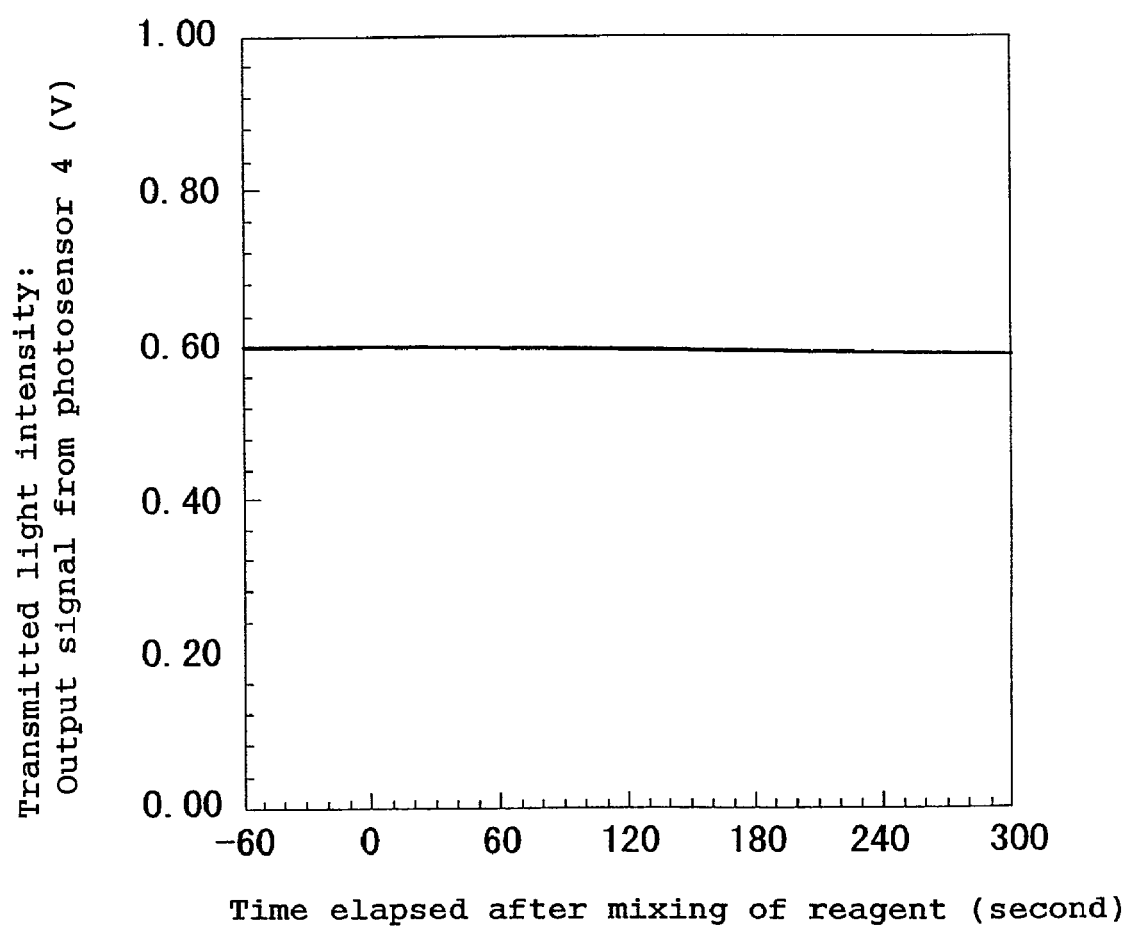
FIG. 16 is a graph showing the change in the transmitted light intensity of a solution to be detected.

The intensities of the scattered light and transmitted light, i.e., the output signals from the photosensors 4 and 5, which were measured using a solution to be detected with a protein concentration of 5 mg/dl with the above method were plotted in FIGS. 15 and 16, respectively. In FIGS. 15 and 16, the abscissa denoted the time elapsed after mixing of the reagent (second), and the ordinate denoted the intensities of the lights detected at the respective photosensors, indicating the change in the intensities of the scattered light or the transmitted light from 60 seconds before to 300 seconds after mixing of the reagent.

Figure 17:
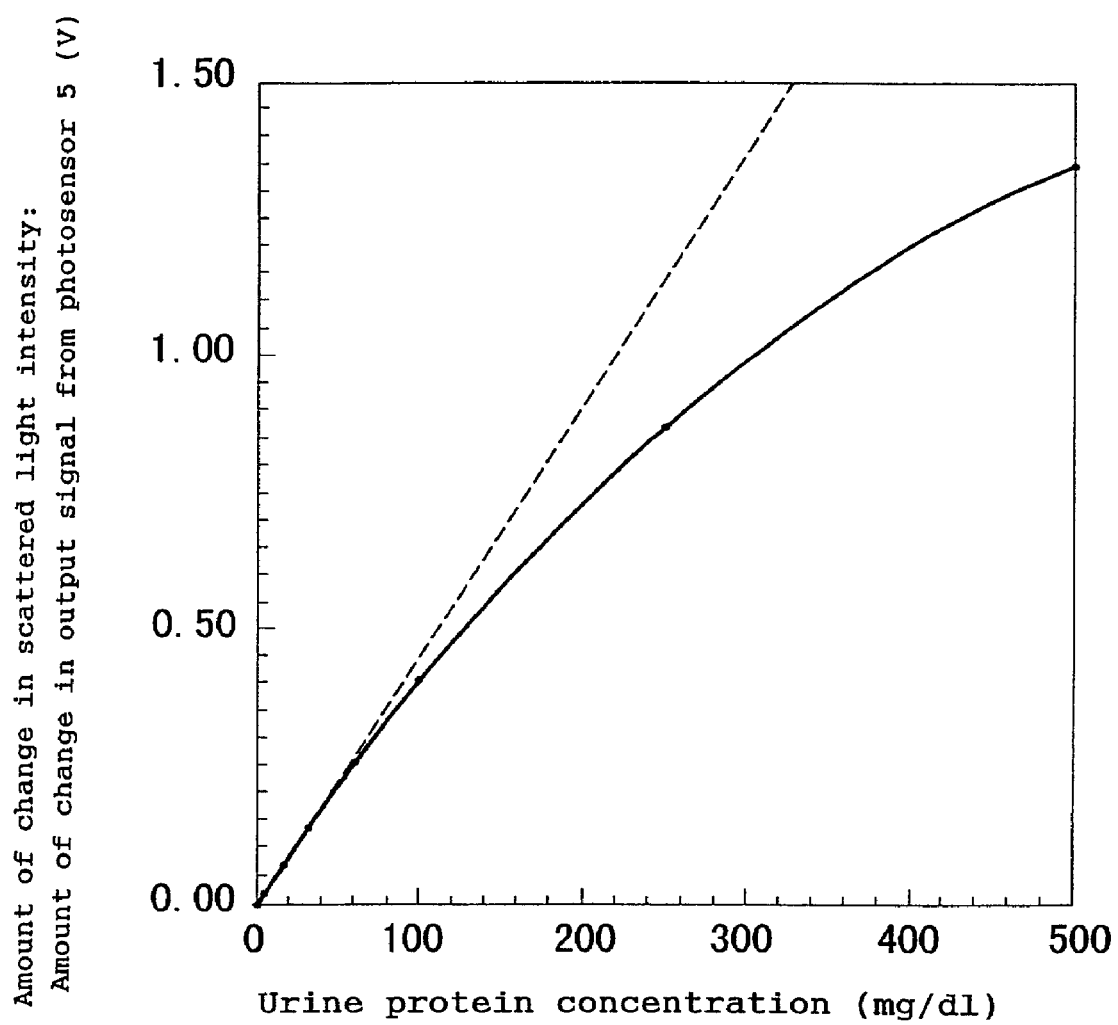
FIG. 17 is a graph showing the relation between the protein concentration in a solution to be detected and the amount of change in the transmitted light intensity.
Figure 18:
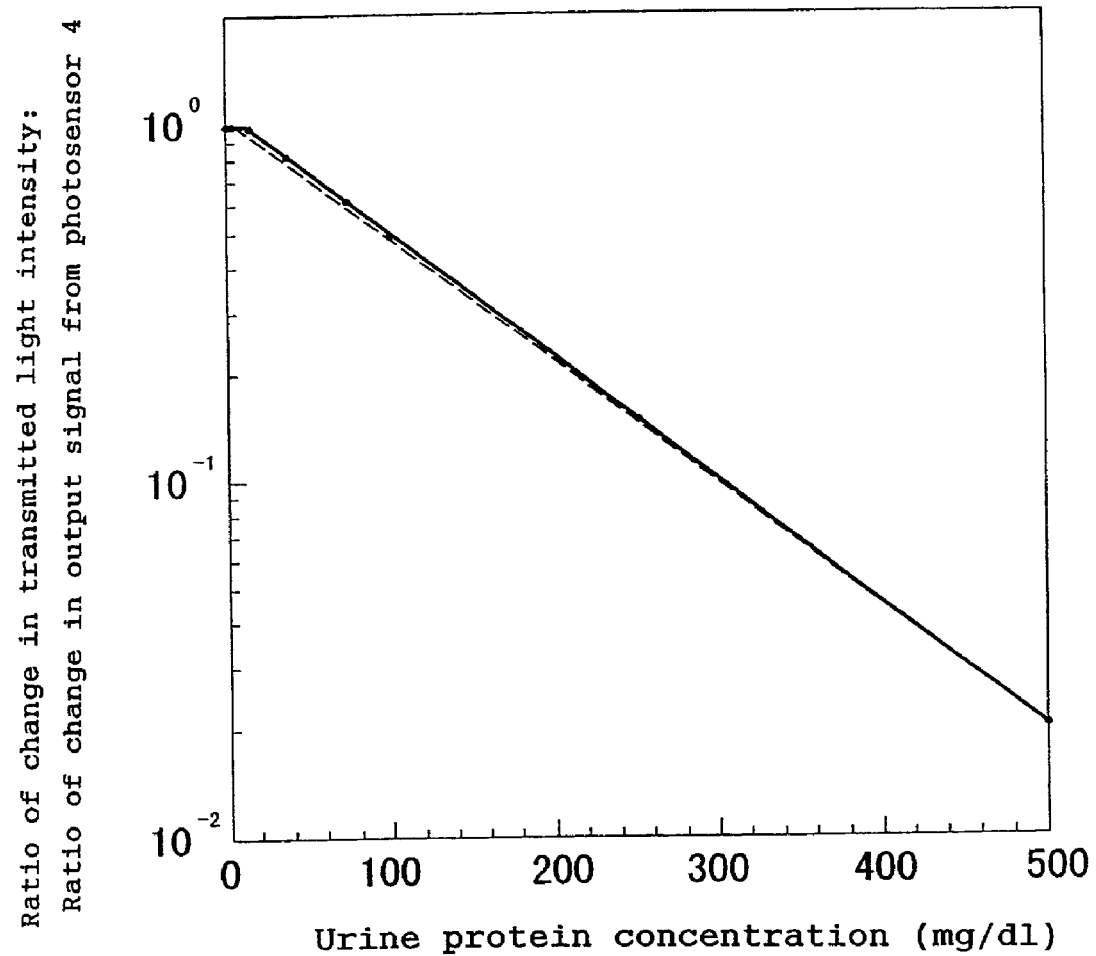
FIG. 18 is a graph showing the relation between the protein concentration in a solution to be detected and the ratio of the transmitted light intensity.

The correlation between the change in the scattered light intensity and the protein concentration, and the correlation between the ratio of the transmitted light intensity and the protein concentration were plotted in FIGS. 17 and 18, respectively. In FIG. 17, the ordinate denoted the difference between the scattered light intensities before and 300 seconds after mixing of the reagent ((the scattered light intensity after mixing of the reagent)–(the scattered light intensity before mixing of the regent)). In FIG. 18, the ordinate denoted the ratio of the transmitted light intensity 300 seconds after mixing of the reagent to that before mixing of the reagent ((the transmitted light intensity after mixing of the reagent)/(the transmitted light intensity before mixing of the reagent)). The results of the measurements of urines with respective concentrations of 0, 15, 30, 60, 100, 250 and 500 mg/dl as a solution to be detected were plotted in FIGS. 17 and 18, in addition to that of the solution to be detected with the protein concentration of 5 mg/dl. In these cases, all of the measured solutions to be detected were optically as transparent as water, and the intensities of the transmitted light and scattered light thereof were the same as those of water.

In FIG. 17, each of the measured values was smoothly connected by a solid line, and the measured value in a protein concentration range of 0 to 30 mg/dl, where the amount of change in the scattered light intensity (the difference between the scattered light intensities before and after mixing of the reagent) changed linearly to the protein concentration, were connected by a dotted line and this line was extended. By using the solid line as a calibration line, the protein concentration could be obtained.

Further, as was evident from those lines, the solid and dotted lines coincided until the protein concentration reached approximately 30 mg/dl, indicating that the amount of change in the scattered light intensity was in proportion to the protein concentration. However, as the protein concentration became higher, the measured value gradually became lower than the corresponding value which was in proportion to the protein concentration. The reason was considered as follows. When the protein concentration became high, so did the probability that the light would be scattered. This increased the probability that the light would be scattered again while the scattered light propagated from the point, where it had arisen, to the outside of the sample cell, thereby decreasing the probability that the scattered light would reach the photosensor 5. Therefore, when determining a protein concentration from the change in the scattered light intensity, the concentration could be more accurately determined in a solution to be detected in the low concentration range (about 30 mg/dl or lower) where the linearity was secured.

A protein concentration in a high concentration range (about 30 mg or higher), which did not agree with the linearity, could be determined by using a calibration line shown by the solid line. It was also confirmed that a protein concentration in the range up to 500 mg/dl could measured directly because the solution to be detected did not become completely saturated.

Herein, when citric acid was not mixed in the aqueous tannic acid solution, there were cases where the scattered light intensity (output signal from photosensor 5) of the solution to be detected with a concentration of 500 mg/dl became about 0 V, resulting in an erroneous operation in which the concentration was assumed as about 0 mg/dl. However, by using a reagent prepared by mixing citric acid in an aqueous tannic acid solution, it was possible to cause turbidity corresponding to the concentration even in a case of the solution to be detected with a high concentration such as 500 mg/dl as shown in this embodiment.

In FIG. 18, the abscissa denoted the protein concentration, and the ordinate (shown in logarithm) denoted the ratio of the transmitted light intensity after mixing of the reagent to that before mixing of the reagent. Each of the measured values was smoothly connected by a solid line, and the measured value in a protein concentration range of 30 to 100 mg/dl, where the logarithm of the transmitted light intensity changed linearly to the protein concentration, were connected by a dotted line and this line was extended. As shown in FIG. 18, in a case of a protein concentration not higher than 30 mg/dl, there were cases where the measured value was not on the dotted line. The reason was considered that the output signal was more vulnerable to influences of various noises because the change in the transmitted light was too small compared with the total output signal. From this, it was confirmed that, when calculating a protein concentration from the transmitted light intensity, the solution to be detected was preferably in a high concentration range (about 30 mg/dl or higher) to avoid the influences of the various noises. It was also confirmed that a protein concentration in the concentration range up to 500 mg/dl could be measured directly because no saturation was observed.

Herein, when citric acid was not mixed in the aqueous tannic acid solution, there were cases where the transmitted light intensity (output signal from photosensor 4) of the solution to be detected with a concentration of 500 mg/dl became about 0.6 V, resulting in an erroneous operation in which the concentration was assumed as about not more than 0 mg/dl. However, by using a reagent prepared by citric acid in an aqueous tannic acid solution, it was possible to cause turbidity corresponding to the concentration even in a case of the solution to be detected with a high concentration, such as 500 mg/dl, as shown in this embodiment.

Therefore, a high accuracy could be ensured by using the dotted lines of FIGS. 17 and 18 thus obtained to determine a concentration in a high concentration range and that in a low concentration range, respectively. As described above, a protein concentration of a solution to be detected could be obtained by measuring an intensity of a transmitted light or that of scattered light before and after mixing of a reagent.

Further, by measuring both of the intensities to determine a concentration of a solution to be detected in a low concentration range from the scattered light intensity, and that in a high concentration range from the intensity of the transmitted light, an accurately measurable concentration range of the solution to be detected, that is, a dynamic range, could be substantially expanded.

According to this embodiment, a protein concentration could be determined using a urine which had been opacified by precipitation of various kinds of salts as a solution to be detected as in the following.

First, a turbid urine with a protein concentration of 30 mg/dl was introduced into the sample cell 3 as a solution to be detected. Herein, the output signal from the photosensor 5 (scattered light intensity) was about 0.05 V. Since the output signal from the photosensor 5 before mixing of the reagent was 0.0 V in the case of the solution to be detected without turbidity as shown in FIG. 15, it could be said that the difference of the output signal indicated the level of turbidity inherent in the solution to be detected of this embodiment. The protein concentration corresponding to this value was from 10 to 12 mg/dl with the solid line shown in FIG. 17 as a calibration line. At this point, the reagent was mixed in the solution to be detected to observe the change in the output signals from the photosensors 4 and/or 5. The output signal from the photosensor 5 when 300 seconds had passed after mixing of the reagent was 0.19 V, and therefore the difference between this signal and that when 0 second had passed after mixing of the reagent was 0.14 V. The protein concentration corresponding to this difference between the output signals (0.14 V) was 30 mg/dl with the solid line shown in FIG. 17 as a calibration line. This concentration was identical with the known concentration which had been measured in advance. From this, it was confirmed that the protein concentration in the turbid solution to be detected could be accurately determined from the difference between the output signals from the photosensor 5 before and after mixing of the reagent by using the calibration line of FIG. 17, which had been obtained from the turbid solution to be detected without turbidity.

As described above, the concentration of a solution could be accurately determined without any influence exerted by turbidity or the like by calculating the concentration of the solution from the difference between the scattered light intensities before and after mixing of the reagent.

Meanwhile, the output signal from the photosensor 4 (transmitted light intensity) before mixing of the reagent was 0.55 V. Since the output signal from the photosensor 4 before mixing of the reagent was 0.6 V in the case of a transparent solution to be detected without turbidity as shown in FIG. 16, the difference could be attributed to the turbidity of the solution. Since the output signal when 300 seconds had passed after mixing of the reagent was 0.45 V, the ratio of these signals was 0.82. The protein concentration corresponding to this ratio of the output signals (0.82) was 30 mg/dl with FIG. 18 as a calibration line. This concentration was identical with the known concentration which had been measured in advance. From this, it was confirmed that the protein concentration in the turbid solution to be detected could be accurately determined by obtaining the ratio of the output signal from the photosensor 4 after mixing of the reagent to that before mixing of the reagent and converting it to a protein concentration by using FIG. 18, which was obtained from the solution to be detected without turbidity, as a calibration line.

In this embodiment, the concentration of the solution was determined from the intensities of the transmitted light and the scattered light immediately before and 300 seconds after mixing of the reagent. However, the lapse of time might be set appropriately according to the measuring apparatus, the characteristics of the solution to be detected or the tannic acid reagent such as the concentration and the like.

In FIGS. 15 to 18, examples were shown in which each of the temperature of the solution to be detected and the reagent, and the ambient temperature were of 40° C. However, it was possible to conduct measurement at a temperature ranging from 0 to 50° C. Therefore, unlike the method using trichloroacetic acid as a reagent, the method in accordance with the present invention enabled measurements to be conducted at a temperature of 25° C. or higher, and could be used at a possible ambient temperature at home.

The pHs of mixed solutions prepared by mixing the urines used as a solution to be detected in this embodiment and the above aqueous tannic acid-citric acid solution reagent were from 2.4 to 3.0. In this embodiment, the reagent was prepared by adding citric acid in the aqueous tannic acid solution. However, the similar effect could be obtained by using any acid, which could regulate the pH of the solution after mixing the solution to be detected and the reagent therein to 1.5 to 5.8. The similar effect could also be obtained by adding an acid in the solution to be detected to regulate the pH of the solution after mixing of the reagent to 1.5 to 5.8. Herein, when the kind or the amount of acid to be mixed in the solution to be detected and/or in the reagent was different, calibration lines (corresponding to the dotted lines and solid lines of FIGS. 17 and 18) changed. Therefore, it was necessary to form different calibration lines (corresponding to the dotted lines and solid lines of FIGS. 17 and 18) in such a case. When the pH was not in the above-mentioned range, the protein might not coagulate at all, so that it was impossible to conduct a stable measurement. Thus, it was practically preferable to conduct the measurement within the pH range.

Herein, in the case where the solution to be detected was a urine, it was particularly practicable to select one acid from the group consisting of potassium hydrogen phthalate, acetic acid, citric acid and ascorbic acid as an acid to be mixed in the reagent and/or in the solution to be detected, because these acids are easy to give an appropriate buffer capacity, low cost, easy to handle, and moreover, reduce the possibility of inducing the precipitation of a phosphate, a carbonate or the like and thus are highly practicable.

In this embodiment, an aqueous tannic acid-citric acid solution with a concentration of tannic acid of $3 \times 10^{-4}$ ($\approx 0.05$ g/dl) and that of citric acid of 5 g/dl used as a reagent and a solution to be detected were mixed at a volume ratio of 0.1 to 0.9 to regulate the concentration of tannic acid to $3 \times 10^{-5}$ ($\approx 5 \times 10^{-3}$ g/dl) and that of citric acid to 0.5 g/dl after mixing of the reagent. However, even when each of these concentrations after mixing of the reagent were not in the above ranges, the protein concentration could be measured by forming calibration lines corresponding to the concentrations of tannic acid and citric acid after mixing of the reagent in the solution to be detected as long as the tannic acid concentration of $3 \times 10^{-5}$ to $3 \times 10^{-2}$ M ($\approx 5 \times 10^{-3}$ to 5 g/dl) and the pH was in the range of 1.5 to 5.8 after mixing of the reagent. When the tannic acid concentration was lower than the above range, there were cases where the protein did not coagulate, so that it was difficult to conduct a stable measurement. When the tannic acid concentration was higher than the above range, the coagulated protein rapidly precipitated to cause a nonuniform turbidity, preventing the solution to be detected from opacifying corresponding to the concentration around the region where the substantially parallel light 2 passed, so that it was difficult to conduct a stable measurement. Therefore, it was practically preferable that measurement be conducted within the above concentration range.

In this embodiment, the mixing ratio of the solution to be detected to the reagent was 9:1. However, even when concentrations of tannic acid and citric acid after mixing of the reagent were in the same range as in the above example, the calibration line changed if the mixing ratio was different, and therefore it was necessary to form a calibration line corresponding to the mixing ratio. Herein, if the mixing ratio of the solution to be detected and the reagent increased, for example, to 1:1, the turbidity of the solution to be detected became low compared with the solution to be detected with the same protein concentration. Therefore, if the tannic acid concentration after the mixing of the reagent was kept constant, it was advantageous to use an aqueous tannic acid-citric acid solution reagent with a high tannic acid concentration, because lowering of the mixing ratio was effective to simply improve the sensitivity of the solution to be detected to the protein concentration. Here, it was confirmed that a tannic acid concentration where neither precipitation nor denaturation occurred at a temperature of 0 to 40° C., which was a possible ambient temperature at home where the reagent would be used, was not higher than 1.5 M ($\approx$250 g/dl). Therefore, it was practically advantageous to set the tannic acid concentration of the aqueous tannic acid-citric acid solution reagent to be not higher than this concentration.

Similarly, it was also advantageous to use a citric acid with high concentration. However, it was necessary that the citric acid concentration was not higher than the concentration where neither precipitation nor denaturation occurred at a temperature from 0 to 40° C., which was the above ambient temperature. Herein, it was also necessary that the concentration was in the range where no precipitation or denaturation due to an interaction between tannic acid and citric acid occurred.

Embodiment 7

The presence or absence of a obstruction of measurement due to a suspending particle such as a bubble in a solution to be detected was detected by measuring output signals from the photosensors 4 and 5 and comparing the measured values using the apparatus shown in FIGS. 5 and 6 with the same method as in Embodiment 2. When any suspending particle such as a bubble was present in a solution to be detected and entered into an optical path of the substantially parallel light 2, the substantially parallel light 2 was highly scattered, thereby obstructing an accurate measurement of intensities of the transmitted light and/or the scattered light. In this case, the transmitted light intensity substantially decreased. On the other hand, the scattered light intensity either substantially decreased or increased depending on the angle of visibility of the photosensor 5, the location of the suspending particle such as a bubble present in the optical path and the like.

When no obstruction due to a suspending particle such as a bubble was present, there existed a certain relation between the intensities of the scattered light and the transmitted light as shown in FIGS. 17 and 18. For example, the difference between the scattered light intensities before and after mixing of the aqueous tannic acid-citric acid solution reagent was 0.14 V and the ratio of the transmitted light intensity after mixing of the reagent to that before mixing of the reagent was 0.82 when the protein concentration of the solution to be detected was 30 mg/dl. However, if the aforementioned obstruction was present, a value which was inconsistent with the above relation was measured. Therefore, the presence or absence of the above-mentioned obstruction could be detected by examining whether or not the protein concentration obtained from the measured value of the photosensor 4 based on the calibration line of FIG. 18 was identical with that obtained from the measured value of the photosensor 5 based on the calibration line of FIG. 17 before and after the mixing of the tannic acid-citric acid reagent.

As described above, according to this embodiment, an obstacle due to a suspending particle such as a bubble could be detected to prevent an erroneous measurement by measuring both of the intensities of the transmitted light and the scattered light before and after mixing of the aqueous tannic acid-citric acid solution reagent, and comparing the intensities. This improved the reliability of a measurement and greatly contributed to a practical effect, enabling a higher reliability and labor saving of measurement and testing.

Embodiment 8

In this embodiment, an angle of rotation of a solution to be detected was measured before mixing therein a reagent, and an aqueous m-galloyl gallic acid-citric acid solution was mixed in a solution to be detected to coagulate the protein thereby to opacify the solution to be detected. The protein concentration was measured from the change in the turbidity after mixing of the reagent, and the concentration of any optical active substance other than protein was determined from the measured values.

Specifically, after measuring an angle of rotation of the solution to be detected, an aqueous m-galloyl gallic acid-citric acid solution reagent with an m-galloyl gallic acid concentration of 0.047 M ($\approx$1.5 g/dl) and a citric acid concentration of 0.3 g/dl and a solution to be detected were mixed at a ratio of 1:49 to measure the transmitted light intensities before and after mixing of the reagent. Herein, the pH of the reagent was about 2.6 to 2.8.

Then, the concentration of protein was obtained from this intensity, and that of any optical active substance other than protein was determined from the protein concentration and the angle of rotation. Herein, the concentration of m-galloyl gallic acid after mixing of the reagent was $9.4 \times 10^{-4}$ M ($\approx$0.03 g/dl) and that of citric acid was 0.006 g/dl. In the following, this will be explained in detail.

A glucose concentration (urine sugar value) and a urine protein concentration were tested by using a urine as a solution to be detected with the apparatuses shown in FIG. 11, which was used in the Embodiment 4 under the conditions similar to those in Embodiment 4.

First, the solution to be detected was introduced into the sample cell 13, whereupon the computer 23 operated the light source 11 and the coil driver 20 to measure an angle of rotation of the solution.

Next, the computer 23 stopped the operation of the coil driver 20, and at the same time started to monitor an output signal from the photosensor 19. Then, the computer 23 controlled the pipette 24 such that the aqueous m-galloyl gallic acid-citric acid solution reagent was mixed in the solution to be detected in the sample cell 13. By assuming the change in the output signals from the photosensor 19 after mixing of the reagent as the change in the transmitted light intensity, a calibration line corresponding to FIG. 18 was formed using urines with respective protein concentrations of 0, 2, 5, 15, 60, 100, and 250 mg/dl as solutions to be detected based on the analyzed ratio of the transmitted light intensity after mixing of the reagent to that before mixing of the reagent with the same method as in Embodiment 6. The calibration line was plotted in FIG. 19.

Figure 19:
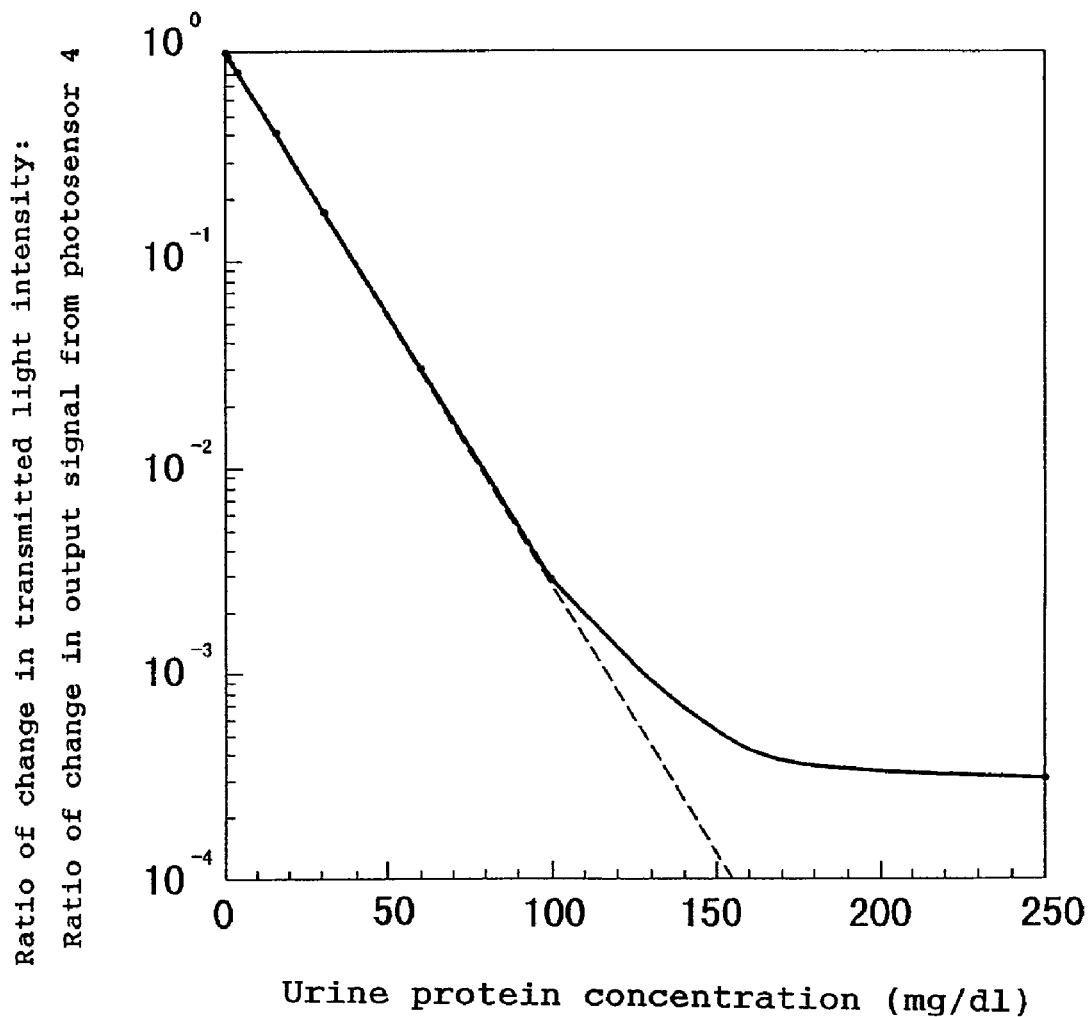
FIG. 19 is a graph showing the relation between the protein concentration in a solution to be detected and the ratio of the transmitted light intensity.

In FIG. 19, the abscissa denoted the protein concentration, and the ordinate (shown in logarithm) denoted the ratio of the transmitted light intensity after mixing of the reagent to that before mixing of the reagent. Each of the measured values was smoothly connected by a solid line, and the measured values in the protein concentration range of 0 to 30 mg/dl, where the logarithm of the transmitted light intensity changed linearly to the protein concentration, were connected by a dotted line and this line was extended. The protein concentration could be determined by using the solid line as a calibration line. As shown in FIG. 19, when the concentration was in the high concentration range (about 100 mg/dl or higher), the solid line was gradually separated from the linear dotted line. This was because, when turbidity became extremely high, the following phenomena occurred as a result of scatterings such as a multiple scattering: a polarization of the substantially parallel light 12 decreased thereby to increase the amount of light transmitting through the analyzer 18; a light which had propagated a plurality of paths reached the photosensor 19; the output signal from the photosensor 19 decreased (about $10^{-4}$ V) to become more vulnerable to the influence of various kinds of noises. Therefore, when determining a protein concentration from the transmitted light intensity, the concentration could be more accurately determined in a concentration range of about 0 to 60 mg/dl where the linearity was secured. A protein concentration in the concentration range exceeding 100 mg/dl, which did not agree with the linearity, could be determined by using a calibration line obtained from the solid line. It was also confirmed that a protein concentration in the concentration range up to 250 mg/dl could be measured directly because the solution to be detected did not become completely saturated.

Herein, when citric acid was not mixed in the aqueous m-galloyl gallic acid solution, there were cases where the ratio of the transmitted light intensity (the ordinate of FIG. 19) became about 0.1, resulting in an erroneous operation in which the concentration was assumed as about 40 mg/dl. However, by using a reagent prepared by mixing citric acid in an aqueous m-galloyl gallic acid solution, it was possible to cause turbidity corresponding to the concentration even in a case of the solution to be detected with a high concentration such as 250 mg/dl as shown in this embodiment.

In the case where a urine with a urine sugar value of 100 mg/dl and a urine protein concentration of 15 mg/dl was used in an example of the above measurement, the angle of rotation was 0.017°. The specific angle of rotation of glucose at this wavelength (670 nm) was 40° deg/cm·dl/kg. Therefore, on the assumption that all of the measured angles of rotations were due to glucose, the glucose concentration, that is, the urine sugar value, was 85 mg/dl. Meanwhile, the protein concentration determined from FIG. 19 was 15 mg/dl because the ratio of the transmitted light was 0.41. Since the specific angle of rotation of the protein was −40° deg/cm·dl/kg, the angle of rotation due to protein was at −0.003°. Therefore, the true angle of rotation due to glucose was calculated at 0.02° by subtracting −0.003° from the above-mentioned 0.017° and the glucose concentration corresponding thereto was calculated at 100 mg/dl.

In the case where a urine with a urine sugar value of 50 mg/dl and a urine protein concentration of 80 mg/dl was used in an another example of the above measurement, the angle of rotation in a urine was −0.006°. The specific angle of rotation of glucose at this wavelength (670 nm) was 40° deg/cm·dl/kg. Therefore, on the assumption that all of the measured angles of rotations were due to glucose, the glucose concentration was calculated at 0 or lower, which was not identical with the measured value. Meanwhile, the protein concentration determined from FIG. 19 was 80 mg/dl because the ratio of the transmitted light was $8\times10^{-3}$. Since the specific angle of rotation of the protein was −40° deg/cm·dl/kg, the angle of rotation due to protein was at −0.016°. Therefore, the true angle of rotation due to glucose was calculated at 0.01° by subtracting −0.016° from the above-mentioned −0.006° and the glucose concentration corresponding thereto was calculated at 50 mg/dl.

From this, according to this embodiment, it was confirmed that a urine sugar value and a urine protein concentration could be accurately determined at the same time by measuring the angle of rotation of the solution to be detected before mixing of the aqueous m-galloyl gallic acid-citric acid solution reagent and the ratio of the transmitted light intensity after mixing of the reagent to that before mixing of the reagent.

As described above, this embodiment could determine concentrations of protein and glucose, which was another optical active substance besides protein, at the same time and therefore was particularly practicable when a solution to be detected was a urine. This will be described in the following.

When a urine protein concentration was normal, glucose was the predominant optical active substance in the urine. Therefore, a urine sugar value could be roughly examined by measuring the angle of rotation of the urine. However, a urinalysis could be conducted more accurately by determining the urine protein concentration with a measuring method other than the one based on the angle of rotation. The reason was considered that the angle of rotation of the urine obtained by such method included the angle of rotation due to glucose and that due to protein because protein as well as glucose was an optical active substance.

Therefore, as shown in this embodiment, the urine sugar value and the urine protein concentration could be accurately determined by obtaining the protein concentration from the change in the optical characteristics after mixing of the reagent, and correcting the measured angle of rotation based on the protein concentration thus measured.

Incidentally, when the reagent was mixed in the solution to be detected before measuring the angle of rotation thereof, the protein component coagulated to prevent the light from transmitting through the solution to be detected, or the protein denatured to change the angle of rotation, and therefore it was not possible to accurately determine the urine sugar value and the urine protein concentration.

In this embodiment, an example was shown in which the angle of rotation and the transmitted light intensity were measured using a light with a wavelength of 670 nm. In general, a specific angle of rotation of a substance increases with a decrease of the wavelength until the wavelength reaches the one where the absorbance inherent in the substance (around 180 nm, in a case of glucose) begins. Moreover, turbidity due to the coagulation of protein increases with a decrease of the wavelength. For this reason, an accuracy of measurement sometimes deteriorated when conducting the measurement with a light having a wavelength of 500 nm or shorter. Therefore, in terms of the sensitivity, it was advantageous to use a light with a shorter wavelength when measuring the angle of rotation, the intensities of the scattered light and transmitted light.

However, when a solution to be detected is urine, a light with a wavelength not longer than 500 nm is absorbed by a dye contained in the urine such as urochrome. measurement less accurate. Therefore, it was practicable to use a light with a wavelength of not shorter than 500 nm when conducting the above measurement.

In this embodiment, the mixing ratio of the solution to be detected to the reagent was 49:1. However, even in the case where a concentration of m-galloyl gallic acid-citric acid after mixing of the reagent was the same as that of the above example, the calibration line changed if the mixing ratio was different. Therefore, it was necessary to form the calibration line corresponding to the mixing ratio. Herein, as the mixing ratio of the solution to be detected and the reagent increased, for example, to 1:1, the turbidity of the solution to be detected became low compared with the solution having the same concentration. Therefore, if the m-galloyl gallic acid concentration after mixing of the reagent was kept constant, it was advantageous to use a regent with a high concentration of m-galloyl gallic acid, because lowering of the mixing ratio was effective to simply improve the sensitivity of the solution to be detected to the protein concentration. Here, it was confirmed that a m-galloyl gallic acid concentration where neither deposition nor denaturation occurred at a temperature of 0 to 40° C., which was a possible ambient temperature at home, was not higher than 7.8 M ($\approx$250 g/dl). Accordingly, a concentration of the aqueous m-galloyl gallic acid solution reagent was set to be not higher than this concentration.

The pHs of mixed solutions prepared by mixing aqueous protein solutions (serum albumin) with respective concentration of 0, 2, 5, 15, 60, 100 and 250 mg/dl and the above aqueous m-galloyl gallic acid-citric acid solution reagent were 4.5 to 5.8. In this embodiment, the reagent was prepared by adding citric acid in the aqueous m-galloyl gallic acid solution. However, the similar effect could be obtained by using any acid capable of regulating the pH of the solution after mixing the solution to be detected and the reagent to 1.5 to 5.8. The similar effect could also be obtained by adding an acid in the solution to be detected to regulate the pH of the solution after mixing of the reagent to 1.5 to 5.8. Herein, if the kind or the amount of acid to be mixed in the solution to be detected and/or in the reagent was different, a different calibration line (corresponding to the dotted line and solid line of FIG. 19) was obtained, and therefore it was necessary to form the calibration line (corresponding to the dotted line and solid line of FIG. 19). If the pH of the solution after mixing of the reagent was not in the above range, there were cases where the protein did not coagulate at all, so that it was impossible to conduct a stable measurement. Therefore, it was practically preferable to conduct the measurement within the above pH range.

Herein, when the solution to be detected was a urine, it was particularly useful to select one acid from the group consisting of potassium hydrogen phthalate, acetic acid, citric acid and ascorbic as an acid to be mixed in the reagent and/or in the solution to be detected, because these acids are easy to give an appropriate buffer capacity, low cost, easy to handle, and moreover, reduce the possibility of inducing the precipitation of a phosphate, a carbonate or the like and thus are highly practicable.

In this embodiment, the concentration of m-galloyl gallic acid in the reagent was 0.047 M ($\approx$1.5 g/dl). Since the mixing ratio of the reagent to the solution to be detected was 49:1, the concentration of m-galloyl gallic acid after mixing of the reagent was $9.4\times10^{-4}$ M ($\approx$0.03 g/dl). However, the protein concentration could be measured at any concentration in the range of $5\times10^{-3}$ to 5 g/dl by forming a calibration line (corresponding to the dotted and solid lines of FIG. 19) corresponding to the m-galloyl gallic acid concentration after mixing of the reagent. When the m-galloyl gallic acid concentration was lower than the above range, there were cases where the protein did not coagulate, and therefore it was difficult to conduct a stable measurement. When the m-galloyl gallic acid concentration was higher than the above range, the coagulated protein rapidly precipitated to cause a nonuniform turbidity, preventing the solution to be detected from opacifying corresponding to the concentration around the region where the substantially parallel light 2 passed, so that it was difficult to conduct a stable measurement. Therefore, it was practically preferable that measurement be conducted within the above concentration range.

As set forth above, according to the present invention, a protein concentration can be measured at a temperature from 0 to 40° C., which is a possible ambient temperature at home. Moreover, by mixing an acid in a reagent, a protein concentration in a high concentration range (approximately 250 to 500 mg/dl or higher) can also be measured. Further, a measurable concentration range of a solution to be detected can be expanded, and at the same time the presence or absence of any obstructions to the measurement due to a suspending particle such as a bubble can be detected. As a result, a protein concentration in a solution to be detected can be determined with high accuracy. Furthermore, it is possible to carry out a highly accurate, practicable and labor saving measurement of a concentration of a solution, particularly a urine protein concentration.

Further, according to the present invention, it is possible to detect both of the concentrations of protein and any optical active substance other than protein in a solution to be detected. In the case where a solution to be detected is a urine, since a urine protein concentration and a urine sugar value can be accurately determined at the same time, the steps required for urinalysis can be substantially simplified, thereby greatly contributing to practical effect.

Although the present invention has been described in terms of the presently preferred embodiments, it is to be understood that such disclosure is not to be interpreted as limiting. Various alterations and modifications will no doubt become apparent to those skilled in the art to which the present invention pertains, after having read the above disclosure. Accordingly, it is intended that the appended claims be interpreted as covering all alterations and modifications as fall within the true spirit and scope of the invention.

What is claimed is:

1. A method for measuring a concentration of protein, comprising the steps of:
   (a) measuring intensities of at least a transmitted light and a scattered light of a solution to be detected before and after mixing therein at least one reagent selected from the group consisting of tannin, tannic acid and m-galloyl gallic acid, and
   (b) determining a concentration of protein in said solution to be detected based on said intensities,
   wherein the protein concentration in said solution to be detected is determined based on the intensities of said transmitted light and said scattered light in said step (b).

2. A method for measuring a concentration of protein, comprising the steps of:
(a) measuring intensities of at least a transmitted light and/or a scattered light of a solution to be detected before and after mixing therein at least one reagent selected from the group consisting of tannin, tannic acid and m-galloyl gallic acid,
(a') regulating a pH of a solution to be detected to 1.5 to 5.8 after mixing therein said at least one reagent, and
(b) determining a concentration of protein in said solution to be detected based on said intensities.

3. The method for measuring a concentration of protein in accordance with claim 2, wherein the pH of the solution to be detected is regulated by adding a pH controlling agent selected from the group consisting of potassium hydrogen phthalate, acetic acid, citric acid and ascorbic acid in said solution to be detected.

4. A method for measuring a concentration of protein, comprising the steps of:
(a) measuring intensities of at least a transmitted light and/or a scattered light of a solution to be detected before and after mixing therein at least one reagent selected from the group consisting of tannin, tannic acid and m-galloyl gallic acid, and
(b) determining a concentration of protein in said solution to be detected based on said intensities,
wherein a concentration of a reagent in a solution to be detected after mixing therein said at least one reagent is in the range of $5 \times 10^{-3}$ to 5 g/dl.

5. The method for measuring a concentration of protein in accordance with claim 1, wherein a concentration of protein in a solution to be detected in a low concentration range is determined from the intensity of said scattered light, and that of a solution to be detected in a high concentration range is determined from the intensity of said transmitted light.

6. The method for measuring a concentration of protein in accordance with claim 1, further comprising a step of:
(c) detecting the presence or absence of an erroneous measurement due to a suspending particle such as a bubble in said solution to be detected by comparing the intensity of said transmitted light with that of said scattered light.

7. A method for measuring a concentration of a solution, comprising the steps of:
(i) measuring intensities of at least a transmitted light and/or a scattered light of a solution to be detected before and after mixing therein at least one reagent selected from the group consisting of tannin, tannic acid and m-galloyl gallic acid, and
(ii) measuring an angle of rotation of said solution to be detected before mixing therein said at least one reagent,
(iii) determining a concentration of protein in said solution to be detected based on the intensities of at least said transmitted light and/or said scattered light, and
(iv) determining a concentration of any optical active substance in said solution to be detected other than said protein from said concentration of protein and said angle of rotation.

8. The method for measuring a concentration of a solution in accordance with claim 7, further comprising a step of:
(i') regulating a pH of said solution to be detected to 1.5 to 5.8 after mixing therein said at least one reagent.

9. The method for measuring a concentration of a solution in accordance with claim 8, wherein the pH of the solution to be detected is regulated by mixing a pH controlling agent selected from the group consisting of potassium hydrogen phthalate, acetic acid, citric acid and ascorbic acid in said solution to be detected.

10. The method for measuring a concentration of a solution in accordance with claim 7, wherein a concentration of a reagent in a solution to be detected after mixing therein said at least one reagent is in the range of $5 \times 10^{-3}$ to 5 g/dl.

11. A reagent for measuring a concentration of protein to be used in a method for measuring a concentration of protein in which a reagent is mixed in a solution to be detected and a concentration of protein is determined from the resulting turbidity,
wherein said reagent contains at least one selected from the group consisting of tannin, tannic acid and m-galloyl gallic acid,
wherein the pH thereof is regulated to the range of 1.5 to 5.8.

12. The reagent for measuring a concentration of protein in accordance with claim 11, wherein said reagent contains one acid selected from the group consisting of potassium hydrogen phthalate, acetic acid, citric acid and ascorbic acid as a pH controlling agent.

13. The reagent for measuring a concentration of protein in accordance with claim 11, wherein said reagent is an aqueous solution dissolved in water.

14. The reagent for measuring a concentration of protein in accordance with claim 13, wherein the concentration of said reagent in said aqueous solution is 250 g/dl or lower.

15. The reagent for measuring a concentration of protein in accordance with claim 12, wherein the concentration of said pH controlling agent is at the highest possible level as long as said pH controlling agent does not deposit in a temperature range operable for said reagent.

16. A method for measuring a concentration of protein, comprising the steps of:
(a) measuring an intensity of at least a transmitted light and/or a scattered light of a solution to be detected after mixing therein at least one reagent selected from the group consisting of tannin, tannic acid and m-galloyl gallic acid,
(b) regulating a pH of a solution to be detected to 1.5 to 5.8 after mixing therein said at least one reagent, and
(c) determining a concentration of protein in said solution to be detected based on said intensities.

17. A method for measuring a concentration of protein, comprising the steps of:
(a) measuring an intensity of at least a transmitted light and/or a scattered light of a solution to be detected after mixing therein at least one reagent selected from the group consisting of tannin, tannic acid and m-galloyl gallic acid,
(b) regulating the pH of the solution to be detected after mixing therein said at least one reagent by adding a pH controlling agent selected from the group consisting of potassium hydrogen phthalate, acetic acid, citric acid and ascorbic acid in said solution to be detected, and
(c) determining a concentration of protein in said solution to be detected based on said intensities.

18. A method for measuring a concentration of protein, comprising the steps of:
(a) measuring an intensity of at least a transmitted light and/or a scattered light of a solution to be detected after mixing therein at least one reagent selected from the group consisting of tannin, tannic acid and m-galloyl gallic acid, and
(b) determining a concentration of protein in said solution to be detected based on said intensities, wherein a concentration of a reagent in a solution to be detected after mixing therein said at least one reagent is in the range of $5 \times 10^{-3}$ to 5 g/dl.

19. A method for measuring a concentration of protein, comprising the steps of:
    (a) measuring an intensity of at least a transmitted light and a scattered light of a solution to be detected after mixing therein at least one reagent selected from the group consisting of tannin, tannic acid and m-galloyl gallic acid, and
    (b) determining a concentration of protein in said solution to be detected based on said intensities,
    wherein the protein concentration in said solution to be detected is determined based on the intensities of said transmitted light and said scattered light in said step (b).

20. The method for measuring a concentration of protein in accordance with claim 19,
    wherein a concentration of protein in a solution to be detected in a low concentration range is determined from the intensity of said scattered light, and that of a solution to be detected in a high concentration range is determined from the intensity of said transmitted light.

21. The method for measuring a concentration of protein in accordance with claim 19, further comprising a step of:
    (c) detecting the presence or absence of an erroneous measurement due to a suspending particle such as a bubble in said solution to be detected by comparing the intensity of said transmitted light with that of said scattered light.

22. A method for measuring a concentration of a solution, comprising the steps of:
    (i) measuring an intensity of at least a transmitted light and/or a scattered light of a solution to be detected after mixing therein at least one reagent selected from the group consisting of tannin, tannic acid and m-galloyl gallic acid,
    (ii) regulating a pH of said solution to be detected to 1.5 to 5.8 after mixing therein said at least one reagent,
    (iii) measuring an angle of rotation of said solution to be detected before mixing therein said at least one reagent,
    (iv) determining a concentration of protein in said solution to be detected based on the intensities of at least said transmitted light and/or said scattered light, and
    (v) determining a concentration of any optical active substance in said solution to be detected other than said protein from said concentration of protein and said angle of rotation.

23. A method for measuring a concentration of a solution, comprising the steps of:
    (i) measuring an intensity of at least a transmitted light and/or a scattered light of a solution to be detected after mixing therein at least one reagent selected from the group consisting of tannin, tannic acid and m-galloyl gallic acid,
    (ii) regulating the pH of the solution to be detected after mixing therein said at least one reagent by adding a pH controlling agent selected from the group consisting of potassium hydrogen phthalate, acetic acid, citric acid and ascorbic acid in said solution to be detected,
    (iii) measuring an angle of rotation of said solution to be detected before mixing therein said at least one reagent,
    (iv) determining a concentration of protein in said solution to be detected based on the intensities of at least said transmitted light and/or said scattered light, and
    (v) determining a concentration of any optical active substance in said solution to be detected other than said protein from said concentration of protein and said angle of rotation.

24. A method for measuring a concentration of a solution, comprising the steps of:
    (i) measuring an intensity of at least a transmitted light and/or a scattered light of a solution to be detected after mixing therein at least one reagent selected from the group consisting of tannin, tannic acid and m-galloyl gallic acid,
    (ii) measuring an angle of rotation of said solution to be detected before mixing therein said at least one reagent,
    (iii) determining a concentration of protein in said solution to be detected based on the intensities of at least said transmitted light and/or said scattered light, and
    (iv) determining a concentration of any optical active substance in said solution to be detected other than said protein from said concentration of protein and said angle of rotation,
    wherein a concentration of a reagent in a solution to be detected after mixing therein said at least one reagent is in the range of $5 \times 10^{-3}$ to 5 g/dl.

25. A reagent for measuring a concentration of protein to be used in a method for measuring a concentration of protein in which a reagent is mixed in a solution to be detected and a concentration of protein is determined from the resulting turbidity,
    wherein said reagent contains at least one selected from the group consisting of tannin, tannic acid and m-galloyl gallic acid,
    wherein said reagent contains one acid selected from the group consisting of potassium hydrogen phthalate, acetic acid, citric acid and ascorbic acid as a pH controlling agent.

26. A reagent for measuring a concentration of protein to be used in a method for measuring a concentration of protein in which a reagent is mixed in a solution to be detected and a concentration of protein is determined from the resulting turbidity,
    wherein said reagent contains at least one selected from the group consisting of tannin, tannic acid and m-galloyl gallic acid,
    wherein said reagent is an aqueous solution dissolved in water,
    wherein the concentration of said reagent in said aqueous solution is 250 g/dl or lower.

* * * * *

UNITED STATES PATENT AND TRADEMARK OFFICE
CERTIFICATE OF CORRECTION

PATENT NO. : 6,969,612 B2
DATED : November 29, 2005
INVENTOR(S) : T. Kawamura

It is certified that error appears in the above-identified patent and that said Letters Patent is hereby corrected as shown below:

Title page,
Item [56], References Cited, U.S. PATENT DOCUMENTS, add:
-- 5,104,527     04/1992          Clinkenbeard
   5,543,018     08/1996          Stevens et al.
   5,100,805     03/1992          Ziege et al.
   5,328,850     07/1994          Corey --; and
FOREIGN PATENT DOCUMENTS, add:
-- GB    1 600 139      10/1981 --.

Signed and Sealed this

Fourth Day of April, 2006

JON W. DUDAS
*Director of the United States Patent and Trademark Office*